(12) United States Patent
Koch et al.

(10) Patent No.: US 10,813,324 B2
(45) Date of Patent: Oct. 27, 2020

(54) MATERIALS AND METHODS FOR MODULATING SEED SIZE, SEED NUMBER, AND SEED SUGAR CONTENT IN PLANTS

(75) Inventors: Karen Elaine Koch, Gainesville, FL (US); Sylvia Morais De Sousa, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 469 days.

(21) Appl. No.: 12/599,652

(22) PCT Filed: May 19, 2008

(86) PCT No.: PCT/US2008/064130
§ 371 (c)(1),
(2), (4) Date: Nov. 5, 2010

(87) PCT Pub. No.: WO2008/144653
PCT Pub. Date: Nov. 27, 2008

(65) Prior Publication Data
US 2011/0191909 A1    Aug. 4, 2011

Related U.S. Application Data

(60) Provisional application No. 60/930,803, filed on May 18, 2007, provisional application No. 60/958,605, filed on Jul. 6, 2007.

(51) Int. Cl.
*A01H 1/00*    (2006.01)
*A01H 5/10*    (2018.01)
*A01H 6/46*    (2018.01)

(52) U.S. Cl.
CPC .............. *A01H 6/4684* (2018.05); *A01H 1/00* (2013.01); *A01H 5/10* (2013.01)

(58) Field of Classification Search
CPC .............. C12N 9/0004; C12N 15/8245; C12N 15/8261
See application file for complete search history.

(56) References Cited

U.S. PATENT DOCUMENTS

| 7,029,889 B2 * | 4/2006 | Famodu ................ C12N 9/0006 435/189 |
| 2005/0042722 A1 * | 2/2005 | Famodu et al. .............. 435/69.1 |

OTHER PUBLICATIONS

Teo et al (PNAS 2006 vol. 103(49) p. 18842-18847).*
Friedberg (Brief. Bioinformatics (2006) 7: 225-242).*
Teo et al (PNAS, 2006, 103(49) p. 18842-18847).*
Genbank Accession No. ABA70761.1.*
De Sousa et al (Genbank Accession No. ABA70761.1, first available online Jul. 30, 2006).*
Campbell et al (Phytopathology vol. 87, No. 11, 1997, pp. 1144-1147).*
Ipsilandis et al (The Journal of Agricultural Science / vol. 134 / Issue 02 / Mar. 2000, pp. 191-198).*
Shewry et al (Trends in Food Science & Technology, vol. 18, Issue 4, 2007, pp. 201-209—Available online Jan. 14, 2007).*
Teo et al (PNAS Dec. 2006, 103(49) p. 18842-18847).*
McCarty et al (The Plant Journal (2005) 44, 52-61) (Year: 2005).*
McCarty, Donald R., et al. "Steady-state transposon mutagenesis in inbred maize." The Plant Journal 44.1 (2005): 52-61 (Year: 2005).*
Jauron, Richard. Harvesting Sweet Corn. Iowa State University, University Extension, 1997 (Year: 1997).*
Boyer C.D., Shannon J.C. (1983) The Use of Endosperm Genes for Sweet Corn Improvement. In: Janick J. (eds) Plant Breeding Reviews. Springer, Boston, MA (Year: 1983).*
Archbold, D. D. "Carbohydrate availability modifies sorbitol dehydrogenase activity of apple fruit" *Physiologia Plantarum*, 1999, pp. 391-395, vol. 105.
Bieleski, R. L. and Redgwell, R J. "Sorbitol versus Sucrose as Photosynthesis and Translocation Products in Developing Apricot Leaves" *Aust. J. Plant Physiol.*, 1985, pp. 657-668, vol. 12.
Blakley, R. L. "The Metabolism and Antiketogenic Effectors of Sorbitol. Sorbitol Dehydrogenase" *Biochem.*, 1951, pp. 257-271, vol. 49.
Carey, E. E. et al. "Occurrence of Sorbitol in *Zea mays*" *Phytochemistry*, 1982, pp. 1909-1911, vol. 21, No. 8.
Cheng, L. et al. "Antisense inhibition of sorbitol synthesis leads to up-regulation of starch synthesis without altering $CO_2$ assimilation in apple leaves" *Planta*, 2005, pp. 767-776, vol. 220.
Clancy, M. and Hannah, L. C. "Splicing of the Maize Sh1 First Intron is Essential for Enhancement of Gene Expression, and a T-Rich Motif Increases Expression without Affecting Splicing" *Plant Physiology*, 2002, pp. 918-929, vol. 130.
Doehlert, D. C. "Ketose Reductase Activity in Developing Maize Endosperm" *Plant Physiol.*, 1987, pp. 830-834, vol. 84.
Doehlert, D. C. et al. "Enzymes of Sucrose and Hexose Metabolism in Developing Kernels of Two Inbreds of Maize" *Plant Physiol.*, 1988, pp. 1013-1019, vol. 86.
Doehlert, D. C. and Kuo, T. M. "Sugar Metabolism in Developing Kernels of Starch-Deficient Endosperm Mutants of Maize" *Plant Physiol.*, 1990, pp. 990-994, vol. 92.

(Continued)

*Primary Examiner* — Phuong T Bui
(74) *Attorney, Agent, or Firm* — Saliwanchik, Lloyd & Eisenschenk

(57) ABSTRACT

The subject invention concerns materials and methods for modulating seed size in plants. In one embodiment, seed size is decreased relative to wild type seed by inhibiting or knocking out expression of a sorbitol dehydrogenase (Sdh) gene or the gene product thereof. In another embodiment, seed size is increased relative to wild type seed by increasing expression of an Sdh gene or the gene product thereof. The subject invention also concerns materials and methods for modulating seed number or sugar content in plants. In one embodiment, seed number or sugar content is increased relative to wild type seed by inhibiting or knocking out expression of a sorbitol dehydrogenase (Sdh) gene or the gene product thereof. In another embodiment, seed number or sugar content is decreased relative to wild type seed by increasing expression of an Sdh gene or the gene product thereof.

20 Claims, 13 Drawing Sheets

Specification includes a Sequence Listing.

(56) References Cited

OTHER PUBLICATIONS

Doehlert, D. C. et al. "Gene Expression during Maize Kernel Development" *Seed Science Research*, 1994, pp. 299-305, vol. 4, Abstract only.

Everard, J. D. et al. "Gas Exchange and Carbon Partitioning in the Leaves of Celery (*Apium gravelolens* L.) at Various Levels of Root Zone Salinity" *Plant Physiol.*, 1994, pp. 281-292, vol. 106.

Huber, S. C. and Akazawa, T. "A Novel Sucrose Synthase Pathway for Sucrose Degradation in Cultured Sycamore Cells" *Plant Physiol.*, 1986, pp. 1008-1013, vol. 81.

Koch, K. E. "Source-Sink Relations in Maize Mutants with Starch-Deficient Endosperms" *Plant Physiol.*, 1982, pp. 322-325, vol. 70.

Koch, K. E. and Avigne, W. T. "Postphloem, Nonvascular Transfer in Citrus" *Plant Physiol.*, 1990, pp. 1405-1416, vol. 93.

Koch, K. E. et al. "Sugar Levels Modulate Differential Expression of Maize Sucrose Synthase Genes" *The Plant Cell*, 1992, pp. 59-69, vol. 4.

Koch, K. E. et al. "Multiple paths of sugar-sensing and a sugar/oxygen overlap for genes of sucrose and ethanol metabolism" *Journal of Experimental Botany*, 2000, pp. 417-427, vol. 51.

Koch, K. E. "Sucrose metabolism: regulatory mechanisms and pivotal roles in sugar sensing and plant development" *Current Opinion in Plant Biology*, 2004, pp. 235-246, vol. 7.

Lo Bianco, R. and Rieger, M. "Activities of Sucrose and Sorbitol Metabolizing Enzymes in Vegetative Sinks of Peach and Correlation with Sink Growth Rate" *J. Amer. Soc. Hort. Sci.*, 1999, pp. 381-388, vol. 124, Abstract only.

Lo Bianco, R. et al. "Carbohydrate metabolism of vegetative and reproductive sinks in the late-maturing peach cultivar 'Encore'" *Tree Physiology*, 1999, pp. 103-109, vol. 19.

Loescher, W. H. et al. "Sorbitol Metabolism and Sink-Source Interconversions in Developing Apple Leaves" *Plant Physiol.*, 1982, pp. 335-339, vol. 70.

Maret, W. and Auld, D. S. "Purification and Characterization of Human Liver Sorbitol Dehydrogenase" *Biochemistry*, 1988, pp. 1622-1628, vol. 27.

Marini, I. et al. "Sorbitol Dehydrogenase from Bovine Lens: Purification and Properties" *Archives of Biochemistry and Biophysics*, 1997, pp. 383-391, vol. 340, No. 2.

McCarty, D. R. et al. "Steady-state transposon mutagenesis in inbred maize" *The Plant Journal*, 2005, pp. 52-61, vol. 44.

Merlo, L. and Passera, C. "Changes in carbohydrate and enzyme levels during development of leaves of *Prunus persica*, a sorbitol synthesizing species" *Physiologia Plantarum*, 2006, pp. 621-626, vol. 83, No. 4, Abstract only.

Negm, F. B. and Loescher, W. H. "Detection and Characterization of Sorbitol Dehydrogenase from Apple Callus Tissue" *Plant Physiol.*, 1979, pp. 69-73, vol. 64.

Negm, F. B. and Loescher, W. H. "Characterization and Partial Purification of Aldose-6-phosphate Reductase (Alditol-6-Phasphate: NADP 1-Oxidoreductase) from Apple Leaves" *Plant Physiol.*, 1981, pp. 139-142, vol. 67.

Ng, K. et al. "Sorbitol Dehydrogenase from *Bacillus subtilis*" *The Journal of Biological Chemistry*, 1992, pp. 24989-24994, vol. 267, No. 35.

Noiraud, N. et al. "The Sucrose Transporter of Celery. Identification and Expression during Salt Stress" *Plant Physiology*, 2000, pp. 1447-1455, vol. 122.

Nosarzewski, M. and Archbold, D. "Tissue-specific expression of Sorbitol Dehydrogenase in apple fruit during early development" *Journal of Experimental Botany*, 2007, pp. 1863-1872, vol. 58, No. 7.

Ohto, M. et al. "Control of seed mass by APETALA2" *PNAS*, 2005, pp. 3123-3128, vol. 102, No. 8.

Oura, Y. et al. "Purification and characterization of a $NAD^+$-dependent sorbitol dehydrogenase from Japanese pear fruit" *Phytochemistry*, 2000, pp. 567-572, vol. 54.

Park, S. W. et al. "Molecular cloning and characterization of four cDNAs encoding the isoforms of NAD-dependent sorbitol dehydrogenase from the Fuji apple" *Plant Science*, 2002, pp. 513-519, vol. 162.

Plaxton, W. C. and Podestá, F. E. "The Functional Organization and Control of Plant Respiration" *Critical Reviews in Plant Sciences*, 2006, pp. 159-198, vol. 25, No. 2.

Rolletschek, H. et al. "Positional cues for the starch/lipid balance in maize kernels and resource partitioning to the embryo" *The Plant Journal*, 2005, pp. 69-83, vol. 42.

Shaw, J. R. and Dickinson, D. B. "Studies of Sugars and Sorbitol in Developing Corn Kernels" *Plant Physiol.*, 1984, pp. 207-211, vol. 75.

Swedlund, B. and Locy, R. D. "Sorbitol as the Primary Carbon Source for the Growth of Embryogenic Callus of Maize" *Plant Physiol.*, 1993, pp. 1339-1346, vol. 103.

Teo, G. et al. "Silencing leaf sorbitol synthesis alters long-distance partitioning and apple fruit quality" *PNAS*, 2006, pp. 18842-18847, vol. 103, No. 49.

Webb, K. L. and Burley, J. W. A. "Sorbitol Translocation in Apple" *Science*, 1962, p. 766, vol. 137, No. 3532.

Xu, J. et al. "A Similar Dichotomy of Sugar Modulation and Developmental Expression Affects Both Paths of Sucrose Metabolism: Evidence from a Maize Invertase Gene Family" *The Plant Cell*, 1996, pp. 1209-1220, vol. 8.

Yamada, K. et al. "Cloning of NAD-Dependent Sorbitol Dehydrogenase from Apple Fruit and Gene Expression" *Plant Cell Physiol.*, 1998, pp. 1375-1379, vol. 39, No. 12.

Yamaguchi, H. et al. "Purification and Properties of NAD-Dependent Sorbitol Dehydrogenase from Apple Fruit" *Plant and Cell Physiology*, 1994, pp. 887-892, vol. 35, No. 6, Abstract only.

Zeng, Y. et al. "Rapid Repression of Maize Invertases by Low Oxygen. Invertase/Sucrose Synthase Balance, Sugar Signaling Potential, and Seedling Survival" *Plant Physiology*, 1999, pp. 599-608, vol. 121.

Zhou, R. et al. "Purification and characterization of sorbitol-6-phosphate phosphatase from apple leaves" *Plant Science*, 2003, pp. 227-232, vol. 165.

Zhou, R. et al. "Down-regulation of sorbitol dehydrogenase and up-regulation of sucrose synthase in shoot tips of the transgenic apple trees with decreased sorbitol synthesis" *Journal of Experimental Botany*, 2006, pp. 3647-3657, vol. 57, No. 14.

\* cited by examiner

Kernel A      Kernel B sdh1 gene:
- Map: bin 1
- Coordinate 1.12
- BAC: 0117G10

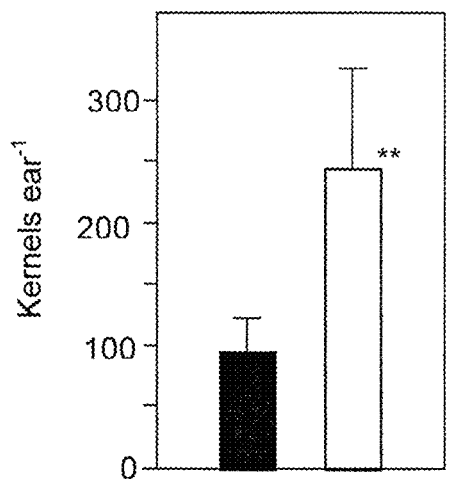
FIG. 11
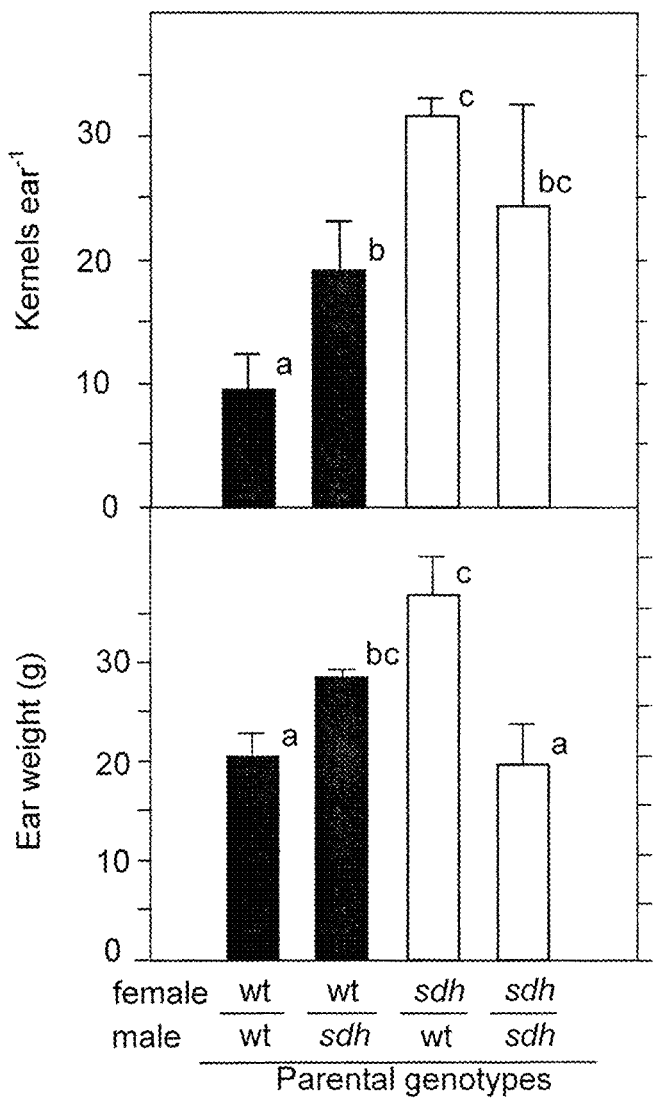
FIG. 12A
FIG. 12B

SEQUENCE LISTING

<160> NUMBER OF SEQ ID NOS: 6

<210> SEQ ID NO 1
<211> LENGTH: 366
<212> TYPE: PRT
<213> ORGANISM: zea mays

<400> SEQUENCE: 1

```
Met Gly Lys Gly Ala Gln Gly Ser Asp Ala Ala Ala Gly Gly Glu
1               5                   10                  15

Val Glu Glu Asn Met Ala Ala Trp Leu Val Ala Lys Asn Thr Leu Lys
            20                  25                  30

Ile Met Pro Phe Lys Leu Pro Pro Val Gly Pro Tyr Asp Val Arg Val
                35                  40                  45

Arg Met Lys Ala Val Gly Ile Cys Gly Ser Asp Val His Tyr Leu Arg
        50                  55                  60

Glu Met Arg Ile Ala His Phe Val Val Lys Glu Pro Met Val Ile Gly
65                  70                  75                  80

His Glu Cys Ala Gly Val Val Glu Glu Val Gly Ala Gly Val Met His
                85                  90                  95

Leu Ser Val Gly Asp Arg Val Ala Leu Glu Pro Gly Val Ser Cys Trp
                100                 105                 110

Arg Cys Arg His Cys Lys Gly Gly Arg Tyr Asn Leu Cys Glu Asp Met
                115                 120                 125

Lys Phe Phe Ala Thr Pro Pro Val His Gly Ser Leu Ala Asn Gln Val
        130                 135                 140

Val His Pro Ala Asp Leu Cys Phe Lys Leu Pro Asp Gly Val Ser Leu
145                 150                 155                 160

Glu Glu Gly Ala Met Cys Glu Pro Leu Ser Met Gly Val His Ala Cys
                165                 170                 175

Arg Arg Ala Gly Val Gly Pro Glu Thr Gly Val Leu Val Val Gly Ala
                180                 185                 190

Gly Pro Ile Gly Leu Val Ser Leu Leu Ala Ala Arg Ala Phe Gly Ala
                195                 200                 205

Pro Arg Val Leu Val Val Asp Val Asp Asp His Arg Leu Ala Val Ala
        210                 215                 220

Arg Ser Leu Gly Ala Asp Ala Ala Val Arg Val Ser Pro Arg Val Glu
225                 230                 235                 240

Asp Leu Ala Asp Glu Val Glu Arg Ile Arg Ala Ala Met Gly Ser Asp
                245                 250                 255

Ile Asp Val Ser Leu Asp Cys Ala Gly Phe Ser Lys Thr Met Ser Thr
                260                 265                 270

Ala Leu Glu Ser Thr Arg Pro Gly Gly Lys Val Cys Leu Val Gly Met
        275                 280                 285

Gly His Asn Glu Met Thr Leu Pro Leu Thr Ala Ala Ala Arg Glu
                290                 295                 300

Val Asp Val Val Gly Val Phe Arg Tyr Lys Asp Thr Trp Pro Leu Cys
305                 310                 315                 320

Ile Asp Phe Leu Arg Ser Gly Lys Val Asp Val Lys Pro Leu Ile Thr
                325                 330                 335

His Arg Phe Gly Phe Ser Gln Arg Asp Val Glu Ala Phe Glu Val
        340                 345                 350

Ser Ala Arg Gly Arg Asp Ala Ile Lys Val Met Phe Asn Leu
        355                 360                 365
```

<210> SEQ ID NO 2
<211> LENGTH: 8151
<212> TYPE: DNA
<213> ORGANISM: zea mays

<400> SEQUENCE: 2

```
ggccgcgatt cgcccttctt ccgagaggta agcgacaaaa aaaaaagttg atcctctgta      60
gctgtagtgc gacttggagg gagggagcga gcgatggtgg caggcagcgg aggttggttt     120
ggttgtcttc agttttctcg ttttgctggg tgcggtaaga aacacaccgc acggggccgt     180
gccgtggacc gagagcgacc actgacagcg ccgtgtgcag gccagggagc ccagaacggt     240
ttttagctgg gccgagcgtt gggcgaggcc gagcccctgg gccttgtggc gatcaccatc     300
tgatacgtgg ggttcgccgc tgggcgcacc actcactgga accaggttta ttccacatag     360
tgcggctact tttttataat aatgaaaaaa cgagtgggta ttcggcgagg ttattgttgt     420
ttttggtccc gttgactaaa gactagctgg agctgcgata acgacgacac gtgctcttgt     480
ggtacaacag cagcgcgatc acatacgtat catgttcatg tatctccgca acctgcaacc     540
agaatttgcg tagagaccga tggaattgtt ctttaattag gggtagtaat taatcgtgat     600
tctaatgatt cttcacaaaa atagtaggga actaaataaa ttttatctaa aaataaaatag     660
aaataatgtc tggtcgatta gatgcatatt gtcacactag cagcaatcgg acccgtcacc     720
ctcgcgccca gaaagaaaga aaaaaacggg cagcgtggcg tgtgatttga ttgatcgagg     780
aaagacgaaa aagagggagt gcaatgggca atggccacgg gcaaggcaaa gtgaagtgcc     840
aactgccaag tgggtgacgt cgcactcgcc aaagtggacc gcgcggaccg gttcaacgac     900
cgcgacgccg aggggcaggc tagggtacca tcattcttgt ccatgtcgtc tgagtagggg     960
gtacactagc tagggtgca gattagcaga tatataattt tttttcccaa tagaacagaa    1020
atagctaggg taggggtaga tatataatcc catggatcag atggagctgc ttctagtttt    1080
gttttgtgag acctacatgt cgatctgctg caagaggttg aatcacctgc aggaaatttt    1140
agttcgacga agtgtgaacg tggtggaggt ccgcctttt gacgtacgtg ggggttccta    1200
tactgtctct gttaatgtgc acagaacttc tggctgttac ggaaagtcct tcttagcaag    1260
tttcacttaa attttaaaac tcgcgaatat atgtggtatg cgtaagcggt aagacagata    1320
atagctccga gcagcgagcc acgcggtttt cccggtccac gccacgccac gccacgcctc    1380
caggtccgcg gcggcacagc cgtgccgtgg cccgcggggg agcgacctct ccctcgccgc    1440
cgatcgagcg cgcgccgacg ccgaatcctt ccagtccaat ccagtccgcg ccgatcgact    1500
gttacgggag tcgctgtgat gcatcggtgg cgtggcgtgg cgtcgccgtc gccgatcgac    1560
tcgccgccgc ctgtgttctt tcttcctcga aatagcggtg gatccttgga ccgtgccacg    1620
acgttttaac gggacgaccg ccggtaaatg ccaagggttt taatgtggaa aggcgaccgg    1680
taattgcggc tggattggat tggatgggct cgagctcgac tcgactgaag ctcacgatgt    1740
gtgcgtgggg gccagccaca gccacacctg cgtacaggac aggcgccgtc gagcacgttt    1800
gcttttgggc cgtgcgtggg accggcgcgt cagtgggtct ctctctctct ctcgctcgct    1860
acctgtcacg tggggtacgg tcgtgcgtcg agctgtcagc agtaaacggg aaagagggtt    1920
cccagtgctg ccctggagct acaggtacag tacagagtgt gtacgtacct tgatggcgat    1980
tggcgacatt cttgcaactg cgtacatgca gtatttgtca tgggcatggg ctcatggcgc    2040
catcctgctc tgtccaaacg tatgccttat gcctatccag tgtggcagtg tccaccaacg    2100
cctgctacta ctacacttgt atcgacggca accggccgag tttggactgg acatgatgcc    2160
```

```
atgctaatct taactgccct tcatttcgac cagcgaccaa attaatcgtg cagtgccaat    2220
ggcgacagtc acgcacggaa gtcggaagca gtgctgctgc tggtatggga cgctccattt    2280 cgccttttc agcctcgccg ggatcatctc ctcatctttt tttttcttc cctgtagagc      2340 tcctctaaga gtactcctac tttcaaaact actgttcta gtcccctcgt aaaaattcta     2400
aaaaaatatt atagtttaaa tttgatgata tatagagaga agagggagca tgaggccttt    2460
atggggagag agttttaaa aaatatatgt aattagatca ctgtcgctta ttgatggggc     2520
ggcagacatc tattcgtgta gttttaatt ctggggtata gaattcagat ttcgaatatt     2580
tttataaaat aaaacggaaa agggaagcag tggaactggg ccagatggcc tcctcagtcg    2640
tatcagtcca atcatctaca aggccttcta tcattcgctt gcagcccaag ttgtcccaag    2700
cattgccgaa gcgtgctgat cgcggttgca gtccagccca acctaacctc atgattaagt    2760
ctgttgaact gtaaaaaata ttttttttag aggcgacagg gaacatttt tttacgatag     2820 ggatataaaa catcttttta gagcaagaga tggaggacag ttttcttaga tagagagata    2880
gacagaagat ttctagatca attgaagaag agatagagaa aacatttatt gaagacaaga    2940
gctagagaaa acatttgact atgtgcctat gtgacggtgc gtccaatgga taggtgaggc    3000
ctgcgtcagt tcagataaaa acaaccccct ttttatatt ccagtaatga aattagaaat     3060
tgcagcaggc catgcatcca tcgtgcagct actctatcta caaatctac aaaaaggacg     3120 cgtttccttg gtcgtcatcg cgctgctatc tatcgcaggt cgccatcttc cggacggaat    3180
atcaaaatgc tgtggacgaa acatgagggc accttcggtc gagtcaccca ccgtttcgtg    3240
tgtcacatac ataccagcgt ctcgcgcgca gggatagaaa tagatgtctg gatgggaact    3300
cgaattattc gatccgctaa aacttgtaat atagctatct gtattcattt tttttctaat    3360
ataagtacta ataaatgta ctagaatttg tttttatag ccggtccaaa accgtattgg      3420
ataaacatat aaagtagtcg atattcatct cgagaacaag atataataaa cctatttgaa    3480
agtttttctt ttcgtaacta gtgactaatt atttgactag tttagttgtc catgtatcac    3540 tacggtttt atatatgata tatgttttc tttgtataac gcaaatcaat ataagctgca     3600
attgagacgg tggtttgcat cctaactgct gcatttttt tgatatattc actgacgcgc     3660
gataaatgct tacggagggg aatgatgcat gacgaaactc cgacttgata ttagtaagga    3720
tttaaatagt actaagaata aattgaaact atttacgata tctttcaata ttgatttcat    3780
actattagta tacatgaatt taaaataaat ttagtatttt tctaatttaa tttgaaccta    3840
acgtatctgt tgttgtcaat tatttaata gtctattttt tgggaatata atattgtttt     3900
agttcaatgg taaatattac acaaataata attgattatt tggtatgtct aaatattaaa    3960
tatttatgag taactagctt attttattta agtttattca gtttatctat tgttttatta    4020
aatatccgta tctaatataa tttagtttat ttcaatgtta gagaccatta taaggctatt    4080 ttgatttta tttcatgtta attatcgatg aacttagtca tgaattcta tttatctatg      4140 ttaaatttag caataataca cgcgctggtc tctgagttaa attaagtgaa cattcgaata    4200
gaaacctgaa tccagtatat ttattttgaa ttcgtattca aaaggatttg tactgaatct    4260
agattaaaat atgataagaa gatggtgtcc agatctgatt ccatacgcgt ttcggttgt     4320 ttcggtttcg attactgctc tccagacaga taccgtgccc gacatgcatg ttctaatcac    4380
acgcctcccc gcccactgca tttcgcatca atccagaaga tttcgcagcc aaagcagtat    4440
ccaacggatg aatggtggtc accagcccag cagccctcga ctcgacgacg actctgtgag    4500
```

```
cgcgaccaca ggtcacaggt gcttgcactg cactcatcct ggtggtggag tgatggttca   4560
gttcatcagt tgtggcttgt ggcgccgcgg cgagtggctg cgcgcgtgac tgtttgtttg   4620
gttcactacc tcagttgcca cactttgcct aacttttctg tctaatgtta gttattcaat   4680
tcgaacgact aaccttaggc aaagtgtggt atatttagcc acaaaccaaa catgccaggc   4740
gggaagcgag ccaaggccag gtccaggcca aaaaatctca cgcttcgcct gacgcctgct   4800
cctggtcgtt acagatagag acggataagc atgacagcgc aggccgcgcg cgtggactc    4860 catgcctgca agggacaat  agagatgccg tctgcgtccg cggcggcatc ggcgccggcg   4920 tcacccccg  ctataaatcc gtcgcacccg cccacccacc tgccgtgcca gtgctctcat   4980
ctgcgtacac ggtctccctc ttcctgtcag tagtagagtg agagtgaggc agcgagtagg   5040
agacaagggg aaatgggaa  gggagcgcaa gggagcgatg cggcggcggc gggcggcgag   5100
gtggaggaga acatggcggc gtggctggtt gccaagaaca ccctcaagat catgcccttc   5160
aagctcccgc ccgtcggtac gtgcctcggt tccatccttc tttctcgctg cttattgttt   5220
gctctgttct aggaatcaga gagatcgata agttttttt  ttatcaaatc gatcggtacc   5280
ctgcacctgc agtacagcct tgcaagttgc caagttccca tctttttttg cattgtctta   5340
tcgtgtttgc acgtgctgaa cacgatggcg aatatgtagt caggaatcta tatcgaagat   5400
ttggatcagc gtcagcgttt tcctcccttt tgggatggaa ttagtagggc atgttcttct   5460 tcgttttta  ggaaacggta tgttcttttt attaaaaaaa tctatggtca aaagaagggg   5520
gatattgaac tatttattgc acaaggtagt tacagtatca tcagcactgg atcgcgtgta   5580
caggaaacat cagtgcatct tttccaagat cctaactact ccagcacaag gaacccact    5640 cattcaatag gctagcagaa tattaaccgt gctaatgcta cggttccgaa gagcggggaa   5700
ggagggagga cccggtggtg gcggtgaggg gaggtgtggc agggtcgcgg ggagagagga   5760
gaattgtact atatgtgtga ggcatgagaa agcacgagt  aaagaagaat gatataataa   5820
tatcggttat tacgttttgaa taagaaagag aagggttata ctttaaccgt ttgttttgaa   5880
agtgtgttat gtatatgtgc aatttgtttg atgaatttag aggaggtcat gagttggagg   5940
tgatttggtt agaagtgttt ctcaaagttt agtctggtgg gttgtatatg gggtatagat   6000
atagataaaa ggacagaatt tgcagtaact tcaaagttca gatctgaatt agataaaatc   6060
agtagtgcgc catacagact tgctgttcg  caatttcttt tcgtttactg gagagaattg   6120
catctgtaag gtgtacgtga tattaaaaat gagcatttga gacatgccac tatgaactca   6180
gcgatgcaca gcaccctga  gtgcagccac tcaggaagcc gtcgtttcga gctgcaggaa   6240
tagcttctat agttattaac acggtaacac ccttgctgtt gcacagcgca tatctcagtt   6300
cagaagaact gaactatgt  gtaatgctac tgaggtgcag tttatcaaca gctttcattt   6360
aggacttagg tgtggtggat gtagctgttc caagtagcaa tcaaatacgg cctgaagtgc   6420
taaaacaaaa tagaatatca gaacttttgt aggctggtcg cataccatgt gaggaaattc   6480
tttaggtcgg aagattagta cttattacaa ctgaataata agtatgctga cagtgaattt   6540
tggctggcat tttcaggccc ttatgatgtc cgcgtgcgca tgaaggcagt ggggatttgc   6600
ggcagcgatg tgcactacct cagggtgcgc gatcctatcc gatgtctctg taattctacg   6660
gcgcgggaat tgttgcacgg ctaatggatt tcgacccttt acgcatcatc gattctcgca   6720
ggagatgcgc atcgcgcact tcgtggtgaa ggagccgatg gtgatcgggc acgagtgcgc   6780
gggcgtggtc gaggaggtgg gcgccggcgt gatgcacctg tccgtgggcg accgcgtggc   6840
gctggagccg ggcgtcagct gctggcgctg ccgccactgc aagggcgggc ggtacaacct   6900
```

-continued

```
gtgcgaggac atgaagttct tcgccacccc gccggtgcac ggctcgctgg cgaaccaggt   6960
ggtgcacccg gccgacctgt gcttcaagct ccccgacggt gtgagcctgg aggagggcgc   7020
catgtgcgag ccgctgagca tgggcgtgca cgcgtgccgc cgcgcggggg tggggcccga   7080
gacgggcgtg ctcgtggtgg gcgccggccc catcggcctg gtgtcgctgc tggcggcgcg   7140
ggccttcggc gcgccgcgcg tgttggtcgt ggacgtggac gaccaccgcc tggccgtggc   7200
caggtcgctg ggcgcggacg cggcggtgcg ggtgtcgccc cgcgtggagg acctggcgga   7260
cgaggtggag cgcatccgcg cggccatggg ctcggacatc gacgtcagcc tggactgcgc   7320
cgggttcagc aagaccatgt cgacggcgct ggagtcgacg cggcccggcg ggaaggtgtg   7380
cctggtcggg atgggccaca acgagatgac gctgcccttg acggcggcgg cggcgcggga   7440
ggtgacgtg gtgggcgtgt tccggtacaa ggacacctgg ccgctgtgca tcgacttcct   7500
gcgcagcggc aaggtggacg tcaagccgct catcacccac cgcttcggct tctcgcagcg   7560
ggacgtggag gaggccttcg aggtcagcgc ccgcggccgc gatgccatca agtcatgtt   7620
caacctctag gcgggcaagc cgcctccctc tcggtccagc cgtctaggcg ccgtcgccgt   7680
atgcccctgc ccccacccag gccacaactc ctggaataaa aatgacagaa aagaaacttt   7740
atagttcgat gaatgggcag tttgccgtgg ttttggaata atttggactt cgtctttttt   7800
cgcttctgtt gtcgtaccat tgtcttaatc gatttgtgga ttttgaagtc tccttttatt   7860
gccaaaagtt cgcgagaact aagtactcac tccgttttaa aatcgtatta gttttagttt   7920
tcaattttta tgtctaaatt taaatgtata atgataaacc tagatgcatt tataaaacac   7980
aaatcaagta ttatataaat ctattacttt ttctaaaata aatttaaatt taaggcggtg   8040
ggtattaaat agtgaaagaa aagggagata gccgttttg ttgccaaaag ttactctgca   8100
aaggcctaaa actacatgaa gggaagggcg aatcgcggcc gctaatcaat g             8151
```

<210> SEQ ID NO 3
<211> LENGTH: 1101
<212> TYPE: DNA
<213> ORGANISM: zea mays

<400> SEQUENCE: 3

```
atggggaagg gagcgcaagg gagcgatgcg gcggcggcgg gcggcgaggt ggaggagaac     60
atggcggcgt ggctggttgc caagaacacc ctcaagatca tgcccttcaa gctcccgccc    120
gtcggccctt atgatgtccg cgtgcgcatg aaggcagtgg ggatttgcgg cagcgatgtg    180
cactacctca gggagatgcg catcgcgcac ttcgtggtga aggagccgat ggtgatcggg    240
cacgagtgcg cgggcgtggt cgaggaggtg ggcgccggcg tgatgcacct gtccgtgggc    300
gaccgcgtgg cgctggagcc gggcgtcagc tgctggcgct gccgccactg caagggcggg    360
cggtacaacc tgtgcgagga catgaagttc ttcgccaccc gccggtgca cggctcgctg    420
gcgaaccagg tggtgcaccc ggccgacctg tgcttcaagc tccccgacgg tgtgagcctg    480
gaggagggcg ccatgtgcga gccgctgagc atgggcgtgc acgcgtgccg ccgcgcgggg    540
gtggggcccg agacgggcgt gctcgtggtg ggcgccggcc ccatcggcct ggtgtcgctg    600
ctggcggcgc gggccttcgg cgcgccgcgc gtgttggtcg tggacgtgga cgaccaccgc    660
ctggccgtgg ccaggtcgct gggcgcggac gcggcggtgc gggtgtcgcc ccgcgtggag    720
gacctggcgg acgaggtgga gcgcatccgc gcggccatgg gctcggacat cgacgtcagc    780
ctggactgcg ccgggttcag caagaccatg tcgacggcgc tggagtcgac gcggcccggc    840
```

```
gggaaggtgt gcctggtcgg gatgggccac aacgagatga cgctgcccct tgacggcggcg    900 gcggcgcggg aggtggacgt ggtgggcgtg ttccggtaca aggacacctg gccgctgtgc    960
atcgacttcc tgcgcagcgg caaggtggac gtcaagccgc tcatcaccca ccgcttcggc   1020
ttctcgcagc gggacgtgga ggaggccttc gaggtcagcg cccgcggccg cgatgccatc   1080
aaagtcatgt tcaacctcta g                                             1101

<210> SEQ ID NO 4
<211> LENGTH: 936
<212> TYPE: DNA
<213> ORGANISM: zea mays

<400> SEQUENCE: 4
gtatctaata taatttagtt tatttcaatg ttagagacca ttataaggct attttgattt     60
ttatttcatg ttaattatcg atgaacttag tcatgaaatt ctatttatct atgttaaatt    120
tagcaataat acacgcgctg gtctctgagt taaattaagt gaacattcga atagaaacct    180
gaatccagta tatttatttt gaattcgtat tcaaaaggat ttgtactgaa tctagattaa    240
aatatgataa aagatggtg tccagatctg attccatacg cgtttcggtt tgtttcggtt    300
tcgattactg ctctccagac agataccgtg cccgacatgc atgttctaat cacacgcctc    360
cccgcccact gcatttcgca tcaatccaga agatttcgca gccaaagcag tatccaacgg    420
atgaatggtg gtcaccagcc cagcagccct cgactgacg acgactctgt gagcgcgacc    480
acaggtcaca ggtgcttgca ctgcactcat cctggtggtg gagtgatggt tcagttcatc    540
agttgtggct tgtggcgccg cggcgagtgg ctgcgcgcgt gactgttttgt ttggttcact    600 acctcagttg ccacactttg cctaactttt ctgtctaatg ttagttattc aattcgaacg    660
actaacctta ggcaaagtgt ggtatattta gccacaaacc aaacatgcca ggcgggaagc    720
gagccaaggc caggtccagg ccaaaaaatc tcacgcttcg cctgacgcct gctcctggtc    780
gttacagata gagacggata agcatgacag cgcaggccgc gcggcgtgga ctccatgcct    840
gcaaggggac aatagagatg ccgtctgcgt ccgcggcggc atcggcgccg cgtcacccc    900 ccgctataaa tccgtcgcac ccgcccaccc acctgc                              936

<210> SEQ ID NO 5
<211> LENGTH: 536
<212> TYPE: DNA
<213> ORGANISM: zea mays

<400> SEQUENCE: 5
attgtatgtc ggtgttcgat tactgtactc cgaagatacc gtgcccgaca tgcatgttct     60
aataacacgc ctccccgccc actgcatttc gcatcaatct agaagatttc gcagccaaag    120
cagtatccaa cggatgaatg gtggtcacca gcccagcagc cctcgactcg acgacgactc    180
tgtgagcgcg accacaggtc acaggtgctt gcactgcact catcctggtg gtggtggagt    240
gatggttcag ttcatcagtt gtggcttgtg gcgccgcggc gagtggctgc gcgcgtgaca    300
gactgacagg cgggaagcga gccaaggcca ggtccaggcc aaaaaatctc acgcttcgcc    360
tgacgcctgc tcctggtcgt tacagataga gacggataag catgacagcg caggccgcgc    420
ggcgtggact ccatgcctgc aaggggacaa tagagatgcc gtctgcgtcc gcggcggcat    480
cggcgccggc gtcaccgccc ccgctataaa tccgtcgcac ccgcccaccc acctgc        536

<210> SEQ ID NO 6
<211> LENGTH: 530
```

```
<212> TYPE: DNA
<213> ORGANISM: Artificial sequence
<220> FEATURE:
<223> OTHER INFORMATION: consensus sequence

<400> SEQUENCE: 6
agtgtatgtc ggtttcgatt actgcactcc aaagataccg tgcccgacat gcatgttcta      60
ataacacgcc tccccgccca ctgcatttcg catcaatcca gaagatttcg cagccaaagc     120
agtatccaac ggatgaatgg tggtcaccag cccagcagcc ctcgactcga cgacgactct     180
gtgagcgcga ccacaggtca caggtgcttg cactgcactc atcctggtgg tggagtgatg     240
gttcagttca tcagttgtgg cttgtggcgc cgcggcgagt ggctgcgcgc gtgacagact     300
gacaggcggg aagcgagcca aggccaggtc caggccaaaa aatctcacgc ttcgcctgac     360
gcctgctcct ggtcgttaca gatagagacg gataagcatg acagcgcagg ccgcgcggcg     420
tggactccat gcctgcaagg ggacaataga gatgccgtct gcgtccgcgg cggcatcggc     480
gccggcgtca cccccgcta taatccgtc gcacccgccc acccacctgc                  530
```

MATERIALS AND METHODS FOR MODULATING SEED SIZE, SEED NUMBER, AND SEED SUGAR CONTENT IN PLANTS

CROSS-REFERENCE TO RELATED APPLICATIONS

The present application is the National Stage of International Application Number PCT/US2008/064130, filed May 19, 2008, which claims the benefit of U.S. Provisional Application Ser. No. 60/930,803, filed May 18, 2007, and U.S. Provisional Application Ser. No. 60/958,605, filed Jul. 6, 2007, each of which is hereby incorporated by reference herein in its entirety, including any figures, tables, nucleic acid sequences, amino acid sequences, and drawings.

GOVERNMENT SUPPORT

This invention was made with government support under CAPES Brazil, the USDA-CSREES-National Research Initiative, and the National Science Foundation, USA; CAPES project number 0083062, USDA project number 35318-18394. The government has certain rights in the invention.

BACKGROUND OF THE INVENTION

Sorbitol is a primary end-product for photosynthesis and a major carbohydrate translocated by many economically-important fruit trees. These are mainly members of two Rosaceaeous subfamilies (Pomoideae and Prunoideae), and include apple, pear, peach, cherry, apricot, and plum (Bieleski and Redgwell, 1985; Loescher and Everard, 1996; Oura et al., 2000). Both sorbitol and sucrose are transported from source leaves to sink tissues such as fruit and shoot tips (Bieleski, 1982; Loescher, 1987). In these species, sorbitol accounts for 50-90% of the C fixed and exported from source leaves (Webb and Burley, 1962; Bieleski and Redgwell, 1985). Sorbitol synthesis shares a common hexose-phosphate pool with sucrose synthesis in the cytosol. In source leaves, G6P is first converted to sorbitol 6-phosphate by aldose 6-phosphate reductase (A6PR; EC 1.1.1.200, also called sorbitol-6-phosphate dehydrogenase, S6PDH), followed by hydrolysis of sorbitol 6-phosphate to form sorbitol via sorbitol-6-phosphate phosphatase (SorPP; EC 3.1.3.50). In these systems, A6PR catalyzes the key regulatory step in sorbitol synthesis (Negm and Loescher 1981; Zhou et al., 2003; Park et al., 2002; Yamada et al., 1998).

When sorbitol is transported to sink tissues of apple or related species, it is converted to fructose by sorbitol dehydrogenase (SDH) prior to further metabolism. Sorbitol dehydrogenases are active in plants, animals, and microorganisms (Touster and Shaw 1962; Bieleski, 1982). The enzyme was first purified from rat liver (Blakley, 1951), and has since been purified and characterized from many sources (Maret and Auld, 1988; Ng et al., 1992; Yamagushi et al., 1994; Marini et al., 1997). In plants, SDH was partially purified and characterized from apple callus (Negm and Loescher, 1979) and maize kernels (Doehlert, 1987), followed by subsequent purification from apple fruits (Yamagushi et al., 1994). SDH activity is high in young apple leaves (Loescher et al., 1982), peach leaves (Merlo and Passera, 1991), and in shoot apecies of peach (Lo Bianco et al., 1999a, Lo Bianco et al., 1999b). In these species, SDH is considered a good indicator of sink strength, which is consistent with its active expression in developing apple fruit (Nosarzewski et al., 2004). In sink tissues of apple, levels of SDH mRNAs can also be enhanced by exogenous feeding of sorbitol (Archbold, 1999; Lida et al., 2004; Zhou et al. 2006). Recently, SDH activity was successfully decreased in transgenic apple trees silenced for sorbitol-6-phosphate dehydrogenase (Teo et al., 2005). This change affected fruit quality and also altered long-distance partitioning. An antisense strategy was also used to reduce activity of A6PR, which lowered sorbitol levels in source leaves and increased those of sucrose (Cheng et al., 2005). An additional consequence of this change was a down-regulation of SDH in assimilate-importing shoot tips, and a commensurate up-regulation of sucrose synthase (Zhou et al., 2006).

Sorbitol may also share some functions with other sugar-alcohols. Mannitol, for example has been proposed to function in dissipation of excess reducing power during photosynthesis by celery (Loescher, 1987). This was considered a possible contributor to the unusual photosynthetic features of this plant. Other roles for sugar alcohols have included their function as protectants against osmotic, ionic, and temperature stress (Everard et al., 1994; Noiraud et al., 2000). An intriguing role for sorbitol has also been implicated by studies of in vitro development of somatic maize embryos, where sorbitol was found to be unique among different sugars in its capacity to support growth of embryogenic callus (Swedlund and Locy, 1993).

In maize, the roles of sorbitol remain unclear. It does not appear to have a long-distance transport function, since sorbitol levels are below detection in maize phloem (Zimmerman and Ziegler, 1975). In addition, although sorbitol can be abundant in developing kernels (Carey, 1982; Doehlert and Kuo, 1990), levels drop as the grains mature. Any osmo-protective roles of sorbitol in kernels would thus be limited to periods prior to onset of desiccation tolerance. Nonetheless, significant amounts of photosynthate are partitioned to sorbitol as assimilates enter kernels (Shaw and Dickinson, 1984).

The role of sorbitol dehydrogenase in maize has remained likewise equivocal. Collective evidence suggests that in vivo, SDH activity in the maize kernel may operate in an opposite direction to that observed in sink tissues of apple and related species. Sucrose first arriving at the kernel can be cleaved by either invertase or the reversible sucrose synthase reaction. In either case, fructose is a product (Koch, 2004). Fructose is typically phosphorylated by hexokinase, then used for respiration or polysaccharide biosynthesis. Alternatively, fructose may follow a less well-known fate in kernels, where it can be converted to sorbitol by sorbitol dehydrogenase (SDH, EC 1.1.1.14). SDH is highly active in maize endosperm, but since kernels do not store sorbitol, an intermediary role seems likely. The Km and Vmax of maize sorbitol dehydrogenase (Km [fructose] 136 mM and Km [sorbitol] 8.45 mM; Doehlert, 1987) would favor sorbitol biosynthesis in high-fructose tissues. Also, a negative correlation has been reported between fructose abundance and SDH activity in maize kernels (Doehlert and Kuo, 1990). The preferred direction of SDH will depend largely on the ratio of (fructose+NADH) to (sorbitol+NAD), however, so high NADH content will also favor sorbitol formation.

Relevant to this issue are recent analyses showing very low oxygen levels inside maize kernels (FIG. 1 [from Rolletschek et al., 2005]). Oxygen percentages drop to the level of detection, or below, immediately inside the endosperm. Such an environment has important implications for deposition of protein and starch. The latter remains unaffected, even when exogenous oxygen levels are further depleted (Rolletshek et al., 2005). Although partitioning of photosynthate to embryo lipids requires more oxygen, endosperm biochemistry appears well adapted to its low-oxygen environment. Plant glycolysis is especially versatile in this regard (Plaxton and Podesta, 2006; Koch 2004; Huber and Akazawa, 1986), but supplies of NAD could become limiting under low-O2 conditions. Elevated NADH levels in the maize endosperm would favor a sorbitol-producing role for SDH and its potential dissipation (or balance) of excess reducing power. Any short-distance movement of sorbitol to better-oxygenated areas, such as embryos, could facilitate generation of NADH and fructose for use at those sites. Other endosperm regions may also be locales of sorbitol use, since metabolic gradients in this structure can be marked (Rolletschek et al., 2005).

Work from sorbitol-transporting species has identified a number of sorbitol-handling enzymes, which we have sought in the maize and rice genomes, and tested at the activity level in maize. Our preliminary work has identified an aldose reductase (AR, EC 1.1.1.21) that that may be a candidate for sorbitol degradation in kernels. This AR appears to prefer sorbitol to glucose as a substrate (not shown), hence may have a sorbitol-degrading role. We also found that the SDH enzyme in maize shares a 67% identity with that in apple. However, the maize and rice genomes lack any genes or proteins with sequence similarity to the apple sorbitol-6-phosphate phosphatase or aldose-6-phosphate reductase. Sequence similarities were also lacking for any maize or rice genes that might encode apple-like enzymes of NADP-dependent sorbitol dehydrogenase (converts sorbitol to glucose), an NADP-dependent sorbitol 6-P dehydrogenase (converts sorbitol 6-P to glucose 6-P), or a sorbitol oxidase (converts sorbitol to glucose independent of either NAD or NADP). We did identify a maize aldose reductase (noted above) that we assayed for capactity to convert sorbitol to glucose, and vice-versa (as occurs in mammals and fungi). This AR shares a 40% identity with aldose-6-phosphate reductase, thus indicating an overall family relationship, but potentially very different enzymes. Bioinformatic analysis of the maize Sdh1 gene indicates that it is present as a single copy in the maize genome (Southern blot results not shown), with a single counterpart in rice (chromosome 8), and Arabidospis (chromosome 5).

BRIEF SUMMARY OF THE INVENTION

The subject invention concerns materials and methods for modulating seed size in plants. In one embodiment, seed size is decreased relative to wild type seed by inhibiting or knocking out expression of a sorbitol dehydrogenase (Sdh) gene or the gene product thereof. In another embodiment, seed size is increased relative to wild type seed by increasing expression of an Sdh gene or the gene product thereof. In a specific embodiment, an Sdh gene is overexpressed.

The subject invention also concerns materials and methods for modulating seed number in plants. In one embodiment, seed number is increased relative to wild type seed by inhibiting or knocking out expression of a sorbitol dehydrogenase (Sdh) gene or the gene product thereof. In another embodiment, seed number is decreased relative to wild type seed by increasing expression of an Sdh gene or the gene product thereof. In a specific embodiment, an Sdh gene is overexpressed.

The subject invention concerns materials and methods for modulating seed sugar content in plants. In one embodiment, seed sugar content is increased relative to wild type seed by inhibiting or knocking out expression of a sorbitol dehydrogenase (Sdh) gene or the gene product thereof. In another embodiment, seed sugar content is decreased relative to wild type seed by increasing expression of an Sdh gene or the gene product thereof. In a specific embodiment, an Sdh gene is overexpressed.

BRIEF DESCRIPTION OF THE DRAWINGS

FIG. 4A shows a mostly-hypothetical model for whole kernels, but the first portion (role of SDH) can now be tested. Also, preliminary evidence is consistent with sorbitol transfer from endosperm to embryo (see FIG. 5 and text). FIG. 4B shows how the reversible SDH reaction could also contribute to metabolic cycling with the potential to aid balance of key reactants and/or shuttle them from one site to another. This possibility would include control of pool sizes for potential signaling molecules (like fructose) or redox control (as for NAD/NADH), and could operate in tissues other than seeds (e.g., floral apecies).

FIG. 5A: MS alone, FIG. 5B: sorbitol (87.65 mM), FIG. 5C: mannitol (87.65 mM), FIG. 5D: sucrose (87.65 mM), FIG. 5E: glucose (87.65 mM), and FIG. 5F: fructose (87.65 mM).

FIG. 6A shows an RNA gel blot with a 400 pb SDH probe. An EtBr control is shown in the lower panel. FIG. 6B shows activity of SDH in sample fractions from the same maize kernels assayed at 30° C., pH 9.0, and 2 mM NAD.

FIG. 9A: A. wild type and B. sdh1-mutant kernels incubated with reaction buffer (68 mM sorbitol, 0.15 mM NAD, 0.18 mM nitro blue tetrazolium, 0.06 mM phenazine methasulfate and 50 mM Tris-HCl, pH 8.0). C. wild type and D. sdh1-mutant control reactions incubated with reaction buffer minus sorbitol. Magnified 0.8×. FIG. 9B shows activity of sorbitol dehydrogenase enzyme in wild type and sdh1 maize kernels during endosperm development (10, 15, 20 and 25 DAP) assayed at 30° C., pH 9.0, and 2 mM NAD. Error bars are SEMs of 3 replications.

FIG. 11 shows total kernels per ear on wild-type (wt) (shaded bar) and sdh mutant plants (unshaded bar) in an inbred W22 background. Plants were grown in 30-L containers under 12-h, light-supplemented greenhouse conditions (November-January) in Gainesville, Fla. Totals for wt and sdh mothers (**) differed at the 0.2% level p<0.002, with error bars denoting SEMs. Plant genotypes were verified by PCR. Similar results (not shown) were obtained from subsequent analyses of field-grown plants.

FIG. 12A shows total kernels per ear on wild-type (wt) (shaded bars) and sdh mutant plants (unshaded bars) in an inbred W22 background. Effects of male and female parents are shown as contributions from wild-type (wt) and sdh mutant plants to crosses (denoted at figure base). Similar results (not shown) were obtained from subsequent analyses of field-grown plants. FIG. 12B shows weight of dried ears from the same individuals sampled for kernel number in FIG. 12A. Plants were grown in 30-L containers under 12-h, light-supplemented greenhouse conditions (November-January) in Gainesville, Fla. Means (bars) marked with letters a, b, and c were significantly different at the 3% level (p<0.028), and "a" differed from "c" at the 0.01% level (p<0.0001). Totals for wt and sdh mothers (**) differed at the 0.2% level (p<0.002), with error bars denoting SEMs. All genotypes were verified by PCR. Similar results (not shown) were obtained from subsequent analyses of field-grown plants.

FIG. 13A shows kernels per ear;

FIG. 13B shows kernels per row; FIG. 13C shows rows per ear, and FIG. 13D shows ear length. Plants were grown in 30-L containers under 12-h, light-supplemented greenhouse conditions (November-January) in Gainesville, Fla. Totals for wt and sdh mothers (**) differed at the 0.2% level (p<0.002) for kernels per ear, at the 0.3% level (p<0.0027) for kernels per row, and at the 2% level (p<0.02) for rows per ear. Error bars denote SEMs. All genotypes were verified by PCR. Similar results (not shown) were obtained from subsequent analyses of field-grown plants.

FIG. 14A is a diagram of insert sites for currently-known transposon-induced mutations in sdh1 genes. The W22 mutations have Mu-transposons inserted immediately upstream or downstream of the putative transcription start site (−17 bp for a newly-identified sdh1-2 allele, and +90 bp for the sdh1-1 allele (data in Figures were obtained for the sdh1-1 allele)). Thus far, wildtype Sdh1 sequences are available only from W22 and other non-B73 lines, because the B73 "wildtype" gene (entered into the maize genome as such) is actually a mutant that has a transposon residing at −140 bp relative to the putative transcription start site. Evidence indicates that the W22-sdh1-1 mutation decreases gene function to below detectable levels, and initial results from the B73 allele suggest at least partial dysfunction of its sdh1 gene. FIG. 14B is a comparison of the 5' sequence from the wildtype Sdh1 (Sorbitol dehydrogenase 1) gene of W22 to that of the "wildtype" sdh1 of B73. The B73 sdh1 sequence is shown on the upper line (SEQ ID NO:4), with a portion of the wildtype W22 Sdh1 sequence immediately below it (SEQ ID NO:5). The consensus sequence (SEQ ID NO:6) appears on the third line, and red denotes identical sequences. The transposon insert in the B73 sdh1 gene is shown in black between bp positions 588 and 712. The W22 sdh1-1 and sdh1-2 insert sites would lie at positions 942 and 834, respectively (triangles). The putative transcription start site is at position 852 (arrow), and the translation start site is at 1032 (not shown).

BRIEF DESCRIPTION OF THE SEQUENCES

Figure 1:
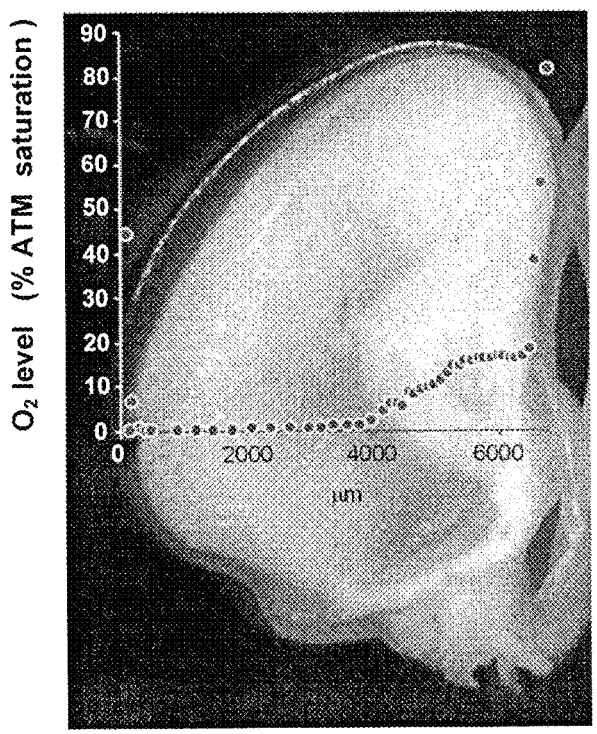
FIG. 1 shows oxygen levels drop to limits of detection or below in endosperm, but not embryos of maize kernels at 300 mg FW. Oxygen microprope path is shown along the x axis. (Figure adapted from Rolletshek et al. 2005). Implications for kernel metabolism are profound.

SEQ ID NO: 1 is an amino acid sequence of a mutant sorbitol dehydrogenase 1 enzyme that can be used according to the present invention.

SEQ ID NO: 2 is a nucleotide sequence that includes a coding region that encodes the amino acid sequence of SEQ ID NO: 1.

SEQ ID NO: 3 is a nucleotide sequence that encodes the amino acid sequence of SEQ ID NO: 1.

DETAILED DISCLOSURE OF THE INVENTION

The subject invention concerns materials and methods for modulating seed size in plants. In one embodiment, seed size is decreased relative to wild type seed by inhibiting or knocking out expression of a Sorbitol dehydrogenase (Sdh) gene or the gene product thereof, or a gene linked to the Sdh gene or the expression thereof. Any means for inhibiting or knocking out expression of a Sdh gene or gene product, or a gene linked thereto, is contemplated within the scope of the present invention. For example, Sdh expression can be inhibited using antisense, short interfering RNA (siRNA), or ribozyme technologies. In one embodiment, Sdh expression can be inhibited in a plant by incorporating a polynucleotide into the plant that provides for an oligonucleotide that is antisense to at least a portion of a nucleotide sequence of an Sdh polynucleotide. In another embodiment, Sdh expression can be inhibited in a plant by incorporating a polynucleotide into the plant that provides for a siRNA molecule capable of directing or mediating RNA interference (RNAi) of Sdh expression. In a further embodiment, Sdh expression can be inhibited in a plant by incorporating a polynucleotide into the plant that encodes a ribozyme that cleaves or inactivates an Sdh RNA.

In a further embodiment, a mutant sdh-encoding polynucleotide is introduced into the genome of a target plant. In one embodiment, the mutant sc/h-encoding polynucleotide encodes a mutant sorbitol dehydrogenase enzyme with decreased enzymatic activity relative to a non-mutated or wild type SDH enzyme. In a specific embodiment, the mutant sorbitol dehydrogenase enzyme comprises the amino acid sequence shown in SEQ ID NO:1, or a fragment, or variant thereof. In one embodiment, the polynucleotide encoding SEQ ID NO:1 comprises the nucleotide sequence shown in SEQ ID NO:2 or SEQ ID NO:3, or a fragment or variant thereof. In another embodiment, a mutant sdh polynucleotide comprises a mutant nucleotide sequence shown in FIG. 14B, or a fragment or variant thereof. In a further embodiment, a mutant sdh gene is incorporated into the genome of a target plant wherein the mutant sdh gene exhibits decreased or no expression of gene transcripts or translation thereof. In one embodiment, a mutation is introduced into an Sdh gene of a plant that results in decreased transcription of the Sdh gene, or decreased translation of sorbitol dehydrogenase mRNA, and/or that results in a protein exhibiting decreased sorbitol dehydrogenase enzymatic activity. In one embodiment, a mutation is introduced in the Sdh gene upstream of the transcription start site and/or downstream of the transcription start site. In one embodiment, a mutation is introduced into or near a regulatory sequence of an Sdh gene, e.g., in a promoter sequence. The mutation may block or inhibit transcription of the Sdh gene sequence, e.g., by blocking or inhibiting binding of transcription factors or polymerase to the Sdh nucleic acid sequence. In a specific embodiment, a mutation is introduced in the protein coding region of the Sdh gene. Mutations include one or more nucleotide(s) insertions, deletions, or substitutions. Methods for introducing mutations are known in the art.

In another embodiment, seed size is increased relative to wild type seed by increasing expression of an Sdh gene or the gene product thereof, or a gene linked to the Sdh gene or the expression thereof. In a specific embodiment, an Sdh gene is overexpressed. Overexpression of Sdh can be achieved using any number of means known in the art and all such means are contemplated within the scope of the invention. For example, a plant can be transformed with multiple copies of a polynucleotide encoding Sdh. In another embodiment, a plant can be transformed with a polynucleotide encoding Sdh, wherein the polynucleotide comprises a promoter and/or other regulatory sequences that provide for increased expression of the polynucleotide, or the Sdh gene product.

In one embodiment, a method of the invention comprises introducing or incorporating a polynucleotide into a plant wherein the polynucleotide or the expression product thereof provides for increased expression of Sdh gene or SDH protein relative to a plant wherein the polynucleotide has not been introduced (e.g., a wild type plant). In one embodiment, a polynucleotide can be introduced that inhibits or decreases degradation of Sdh gene transcripts or gene product. In another embodiment, a polynucleotide can be introduced that encodes an SDH protein that exhibits increased enzymatic activity (for example, via increased resistance to inhibition of enzyme activity). In a further embodiment, a polynucleotide can be introduced that encodes a protein having SDH enzyme activity, wherein the polynucleotide comprises regulatory elements, such as a promoter and/or enhancer sequences, that provide for increased expression of the polynucleotide and/or the protein encoded thereby. In a specific embodiment, the promoter sequence is one that provides for constitutive or tissue-specific (e.g., endosperm) expression. Plants containing the polynucleotide, or progeny thereof, optionally can be screened for increased expression of Sdh gene and/or SDH protein, and/or increased seed or kernel size.

The subject invention also concerns a mutant sdh plant gene, wherein a plant expressing the mutant gene exhibits decreased levels of gene expression and/or the gene product thereof exhibits decreased levels of SDH enzymatic activity.

The subject invention also concerns materials and methods for modulating seed number and sugar content in plants. As used herein, sugar content can refer to sugars, e.g., fructose, sucrose, and glucose, and to sugar alcohols, e.g., sorbitol. In one embodiment, seed number and sugar content is increased relative to wild type seed by inhibiting or knocking out expression of a sorbitol dehydrogenase (sdh) gene or the gene product thereof, or a gene linked to the Sdh gene or the expression of the Sdh gene. Any means for inhibiting or knocking out expression of a Sdh gene or gene product, or a gene linked thereto, is contemplated within the scope of the present invention. In one embodiment, Sdh expression can be inhibited using antisense or siRNA technologies. In a further embodiment, a mutant sdh-encoding polynucleotide is introduced into the genome of a target plant. In one embodiment, the mutant sdh-encoding polynucleotide encodes a mutant sorbitol dehydrogenase enzyme with decreased enzymatic activity relative to a non-mutated or wild type SDH enzyme. In a specific embodiment, the mutant sorbitol dehydrogenase enzyme comprises the amino acid sequence shown in SEQ ID NO:1, or a fragment, or variant thereof. In one embodiment, the polynucleotide encoding SEQ ID NO:1 comprises the nucleotide sequence shown in SEQ ID NO:2 or SEQ ID NO:3, or a fragment or variant thereof. In another embodiment, a mutant sdh polynucleotide comprises a mutant nucleotide sequence shown in FIG. 14B, or a fragment of variant of the sequence. In a further embodiment, a mutant sdh gene is incorporated into the genome of a target plant wherein the mutant sdh gene exhibits decreased or no expression of gene transcripts or translation thereof. In one embodiment, a mutation is introduced into an Sdh gene of a plant that results in decreased transcription of the Sdh gene, or decreased translation of sorbitol dehydrogenase mRNA, and/or that results in a protein exhibiting decreased sorbitol dehydrogenase enzymatic activity. In one embodiment, a mutation is introduced in the Sdh gene upstream of the transcription start site and/or downstream of the transcription start site. In a specific embodiment, a mutation is introduced in the protein coding region of the Sdh gene. Mutations include one or more nucleotide(s) insertions, deletions, or substitutions. Methods for introducing mutations are known in the art. Plants containing a mutant sc/h polynucleotide, or progeny thereof, optionally can be screened for expression of a mutant sdh gene or gene product, and/or increased seed number and/or sugar content.

In another embodiment, seed number and sugar content is decreased relative to wild type seed by increasing expression of an Sdh gene or the gene product thereof, or a gene linked to the Sdh gene or the expression of the Sdh gene. In a specific embodiment, an Sdh gene is overexpressed. Overexpression of Sdh can be achieved using any number of means known in the art. For example, a plant can be transformed with multiple copies of a polynucleotide encoding Sdh. In another embodiment, a plant can be transformed with a polynucleotide encoding Sdh, wherein the polynucleotide comprises a promoter and/or other regulatory sequences that provide for increased expression of the polynucleotide, or the Sdh gene product.

In one embodiment, a method of the invention comprises introducing a polynucleotide into a plant wherein the polynucleotide or the expression product thereof provides for increased expression of Sdh gene or SDH protein relative to a plant wherein the polynucleotide has not been introduced (e.g., a wild type plant). In one embodiment, a polynucleotide can be introduced that inhibits or decreases degradation of Sdh gene transcripts or gene product. In another embodiment, a polynucleotide can be introduced that encodes an SDH protein that exhibits increased enzymatic activity (for example, via increased resistance to inhibition of enzyme activity). In a further embodiment, a polynucleotide can be introduced that encodes a protein having SDH enzyme activity, wherein the polynucleotide comprises regulatory elements, such as a promoter and/or enhancer sequences, that provide for increased expression of the polynucleotide and/or the protein encoded thereby. In a specific embodiment, the promoter sequence is one that provides for constitutive or tissue-specific (e.g., endosperm) expression. Plants containing the polynucleotide, or progeny thereof, optionally can be screened for increased expression of Sdh gene and/or SDH protein, and/or decreased seed or kernel number and/or sugar content.

In one embodiment, a method of the invention comprises introducing a polynucleotide into a plant wherein the polynucleotide or the expression product thereof provides for decreased expression of Sdh gene or SDH protein relative to a plant wherein the polynucleotide has not been introduced (e.g., a wild type plant). In one embodiment, a polynucleotide can be introduced that increases degradation of Sdh gene transcripts or gene product. In another embodiment, a polynucleotide can be introduced that encodes an SDH protein that exhibits decreased enzymatic activity (for example, via decreased resistance to inhibition of enzyme activity). In a further embodiment, a polynucleotide can be introduced that encodes a protein having SDH enzyme activity, wherein the polynucleotide comprises regulatory elements that provide for decreased expression of the polynucleotide and/or the protein encoded thereby. Plants containing the polynucleotide, or progeny thereof, optionally can be screened for decreased expression of Sdh gene and/or SDH protein, or decreased enzymatic activity of the SDH protein, and/or decreased seed or kernel number.

In a further embodiment, multiple copies of a polynucleotide encoding a protein with SDH enzymatic activity are introduced into a plant and stably incorporated into the genome of the plant wherein expression of the multiple copies of the polynucleotide results in increased levels of protein having SDH enzymatic activity.

Embodiments of the invention can preferably provide for expression of a polynucleotide of the invention and any protein encoded thereby in endosperm of a seed or kernel.

Plants used in the methods of the present invention or resulting from the methods of the invention can also optionally comprise other mutations that impact other phenotypic characteristics, such as seed weight, etc. In one embodiment, a plant, plant tissue, or plant cell of the invention also comprises one or more mutations described in U.S. Pat. Nos. 5,589,618; 5,650,557; 5,872,216; 6,069,300; 6,403,863; 6,809,235; 7,312,378; 6,184,438; 6,969,783; and 7,173,165.

The subject invention also concerns materials and methods for modulating sorbitol levels in plants, plant tissue, and plant cells. Modulating expression of an Sdh gene can also increase or reduce levels of sorbitol, a sugar alcohol. Changes in sorbitol levels can have diverse effects. One example is its unique influence on embryo-forming endosperm callus, where, unlike other carbon sources, sorbitol supports only embryogenic calli (not non-embryogenic calli) (Swedlund and Locy, 1993). This indicates that sorbitol, or some aspect of its use, is able to affect cell division, differentiation, or meristem formation. Such roles would be consistent with observed changes in the floral meristem of the sdh mutant(s) (where kernel row number on the ear is established). Levels of sorbitol modulated via an sdh mutation can affect the capacity for regeneration of plantlets after transformation, since this is currently a limiting step in the overall process.

Figure 4A:
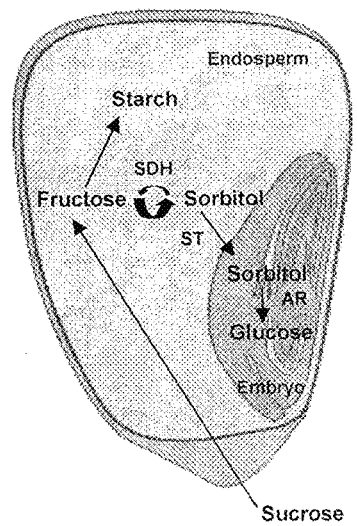
FIGS. 4A-4B show possible scenarios for metabolic roles of sorbitol in maize kernels.
Figure 4B:
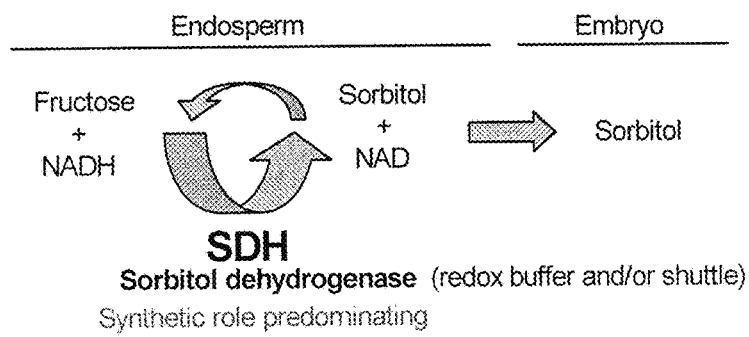
Figure 5A:
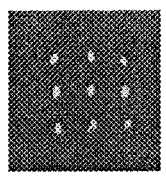
FIGS. 5A-5F show maize embryos (14 DAP) grown in MS (4.3 g/l) salts for 7 days with or without the following supplements.
Figure 5B:
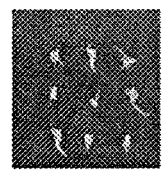
Figure 5C:
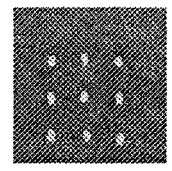
Figure 5D:
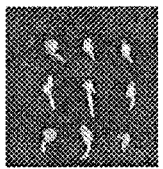
Figure 5E:
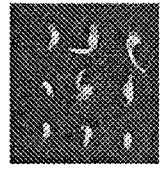
Figure 5F:
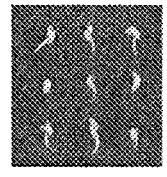

The changes in sorbitol and fructose levels that occur with an sdh mutant provide examples of how altered SDH activity can affect balance of its reactants. As shown in FIGS. 4A and 4B, these reactants include not only fructose (a sugar), sorbitol (a sugar alcohol), but also the nucleotides, NAD and NADH. Changes to any of these reactants (either their pool sizes or flux to other reactions) can have consequences on diverse processes. Fructose is a known signaling molecule, sorbitol effects indicate a similar possibility, and NAD/NADH balance is also known to affect redox status and signaling. The Sdh gene can be used as a tool to alter the levels, production, or use of these constituents.

The subject invention also concerns plants, plant tissue, and plant cells of the invention that exhibit increased or decreased expression of an Sdh encoding polynucleotide or the protein encoded by the polynucleotide, or that express a mutant sdh polynucleotide or a mutant sdh enzyme of the invention, or a fragment or variant thereof. Plant tissue includes, but is not limited to, seed, scion, and rootstock. In one embodiment, the plant, plant tissue, or plant cell is *Zea mays*. In one embodiment, a plant, plant tissue, or plant cell is a transgenic plant, plant tissue, or plant cell. In another embodiment, a plant, plant tissue, or plant cell is one that has been obtained through a breeding program. In one embodiment, the plant, plant tissue, or plant cell is homozygous for a mutant sdh polynucleotide or gene. In another embodiment, the plant, plant tissue, or plant cell is heterozygous for a mutant sdh polynucleotide or gene. The mutant sdh polynucleotide or gene can be provided by the maternal parent and/or the paternal parent. In one embodiment, a plant, plant tissue, or plant cell of the invention is a hybrid plant, plant tissue, or plant cell obtained from breeding a plant comprising a polynucleotide that encodes a mutant sdh enzyme of the invention with a plant that comprises a polynucleotide that encodes a wild type SDH enzyme. In one embodiment, a plant of the invention is an inbred line that has been transformed or bred to exhibit increased or decreased expression of an sorbitol dehydrogenase encoding polynucleotide or the protein encoded by the polynucleotide, or that expresses a mutant sdh polynucleotide or a sdh enzyme of the invention. A plant, plant tissue, or plant cell of the invention comprising a polynucleotide that provides for increased or decreased expression of an Sdh encoding polynucleotide or the protein encoded by the polynucleotide, or that comprises a mutant sdh polynucleotide or a mutant sdh enzyme of the invention, can also comprise other mutations that impact other phenotypic characteristics, such as seed weight, etc. In one embodiment, a plant, plant tissue, or plant cell of the invention also comprises one or more mutations described in U.S. Pat. Nos. 5,589,618; 5,650,557; 5,872,216; 6,069,300; 6,403,863; 6,809,235; 7,312,378; 6,184,438; 6,969,783; and 7,173,165.

The subject invention also concerns an isolated mutant sdh plant gene or polynucleotide, wherein a plant expressing the mutant gene or polynucleotide exhibits decreased levels of SDH enzyme and/or SDH enzymatic activity. In one embodiment, the mutant sdh-encoding polynucleotide encodes an SDH enzyme with decreased enzymatic activity relative to a non-mutated or wild type SDH enzyme. In a specific embodiment, the mutant SDH enzyme comprises the amino acid sequence shown in SEQ ID NO: 1, or a fragment, or variant thereof. In one embodiment, the polynucleotide encoding SEQ ID NO:1 comprises the nucleotide sequence shown in SEQ ID NO:2 or SEQ ID NO:3, or a fragment or variant thereof. In another embodiment, a mutant sdh polynucleotide comprises a mutant nucleotide sequence shown in FIG. 14B, or a fragment or variant of the sequence. Allelic variants of mutant sdh genes or polynucleotides are included within the scope of the invention.

Polynucleotides useful in the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a SDH polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)) can be used. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,639,948; and 5,589,610. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO application No. EP1528104) and those described by Wu et al. (1998), Furtado et al. (2001), and Hwang et al. (2002). Root-specific promoters, such as any of the promoter sequences described in U.S. Pat. No. 6,455,760 or 6,696,623, or in published U.S. patent application Nos. 20040078841; 20040067506; 20040019934; 20030177536; 20030084486; or 20040123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Polynucleotides of the present invention can be composed of either RNA or DNA. Preferably, the polynucleotides are composed of DNA. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode SDH enzymes useful in the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, SDH enzymes of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding an SDH or a mutant sdh of the invention are also encompassed within the scope of the invention.

Substitution of amino acids other than those specifically exemplified or naturally present in an SDH or a mutant sdh enzyme of the invention are also contemplated within the scope of the present invention. For example, non-natural amino acids can be substituted for the amino acids of an SDH or a mutant sdh enzyme, so long as the SDH or a mutant sdh enzyme having the substituted amino acids retains substantially the same functional activity as the SDH or a mutant sdh in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of SDH or a mutant sdh enzyme of the present invention are also encompassed within the scope of the invention.

Amino acids can be generally categorized in the following classes: non-polar, uncharged polar, basic, and acidic. Conservative substitutions whereby an SDH or a mutant sdh enzyme of the present invention having an amino acid of one class is replaced with another amino acid of the same class fall within the scope of the subject invention so long as the SDH or a mutant sdh enzyme having the substitution still retains substantially the same functional activity (e.g., decreased enzymatic activity) as the SDH or a mutant sdh enzyme that does not have the substitution. Polynucleotides encoding an SDH or a mutant sdh enzyme having one or more amino acid substitutions in the sequence are contemplated within the scope of the present invention. Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode enzymatically active SDH enzymes of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of an SDH or a mutant sdh enzyme of the present invention can be generated as described herein and tested for the presence of enzymatic function using standard techniques known in the art. Thus, an ordinarily skilled artisan can readily prepare and test fragments and variants of an SDH or a mutant sdh enzyme of the invention and determine whether the fragment or variant retains functional enzymatic activity relative to full-length or a non-variant SDH or a mutant sdh enzyme.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in. Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

Tm=81.5 C+16.6 Log [Na+]+0.41(% G+C)−0.61(% formamide)−600/length of duplex in base pairs.

Washes are typically carried out as follows:

(1) Twice at room temperature for 15 minutes in 1×SSPE, 0.1% SDS (low stringency wash).

(2) Once at Tm−20 C for 15 minutes in 0.2×SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of polynucleotide sequences of the invention also fall within the scope of the subject invention. The polynucleotide sequence includes both the sense and anti-sense strands either as individual strands or in the duplex.

Plants within the scope of the present invention include monocotyledonous plants, such as, for example, rice, wheat, barley, oats, rye, sorghum, maize, sugarcane, pineapple, onion, bananas, coconut, lilies, turfgrasses, and millet. Plants within the scope of the present invention also include dicotyledonous plants, such as, for example, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, and lettuce. Herb plants containing a polynucleotide of the invention are also contemplated within the scope of the invention. Herb plants include parsley, sage, rosemary, thyme, and the like.

Techniques for transforming plant cells with a gene are known in the art and include, for example, *Agrobacterium* infection, biolistic methods, electroporation, calcium chloride treatment, PEG-mediated transformation, etc. U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention.

The subject invention also concerns methods for producing a plant that exhibits increased or decreased SDH content and/or enzymatic activity relative to a wild type plant, wherein a polynucleotide encoding an SDH or a mutant sdh enzyme of the present invention is introduced into a plant cell and the polypeptide(s) encoded by the polynucleotide(s) is expressed. In one embodiment, the polynucleotide or polynucleotides is incorporated into the genome of the plant cell and a plant is grown from the plant cell. In a preferred embodiment, the plant grown from the plant cell stably expresses the incorporated polynucleotide or polynucleotides.

The subject invention also concerns methods and materials for selecting for plants having increased or decreased seed size, seed number and/or sugar content. In one embodiment, a mutant sdh gene or polynucleotide that encodes an SDH enzyme having decreased enzymatic activity relative to a wild type or non-mutated SDH is utilized as a genetic marker. In a specific embodiment, the SDH enzyme comprises an amino acid sequence of SEQ ID NO: 1, or a fragment or variant thereof. In a specific embodiment, the mutant sdh gene or polynucleotide comprises a nucleotide sequence of SEQ ID NO: 2 or SEQ ID NO: 3, or a mutant sequence shown in FIG. 14B, or a fragment or variant thereof. Methods of the invention comprise determining whether a plant, plant tissue, or plant cell contains a mutant sdh gene or polynucleotide of the invention, and/or determining whether a plant, plant tissue, or plant cell comprises or expresses a mutant SDH enzyme of the present invention. In one embodiment, the presence of a mutant sdh gene or polynucleotide is determined by screening nucleic acid from the plant, plant tissue, or plant cell for hybridization with a nucleic acid probe (e.g., an oligonucleotide of the invention) that hybridizes with a mutant sdh gene or polynucleotide of the invention. In another embodiment, the presence of a mutant sdh gene or polynucleotide is determined by restriction fragment length polymorphism (RFLP) analysis, by polymerase chain reaction (PCR) amplification of specific sdh nucleic acid sequences, or by sequencing sdh-encoding nucleic acid from the plant, plant tissue, or plant cell and identifying whether the gene or polynucleotide comprises a mutant sequence that provides for decreased sdh mRNA levels or decreased SDH enzymatic activity.

The subject invention also concerns methods for marker assisted selection and breeding in plants using a gene or polynucleotide that provides for modulated expression (increased or decreased) of Sdh or the gene product thereof for selecting for plants, plant tissue, or plant cells that exhibit a phenotypic characteristic of interest, e.g., increased or decreased seed size, seed number, sugar content, etc. Methods for marker assisted selection are known in the art. In one embodiment, a method uses a mutant sdh gene or polynucleotide of the invention that encodes a sorbitol dehydrogenase enzyme that is non-functional or that exhibits decreased enzymatic activity relative to a non-mutant SDH enzyme, or wherein the mutant sdh gene or polynucleotide provides for decreased or no expression of gene transcripts or translation of gene transcripts.

The subject invention also concerns oligonucleotide probes and primers, such as polymerase chain reaction (PCR) primers, that can hybridize to a coding or non-coding sequence of a polynucleotide of the present invention. Oligonucleotide probes of the invention can be used in methods for detecting and quantitating nucleic acid sequences encoding a sorbitol dehydrogenase. Oligonucleotide primers of the invention can be used in PCR methods and other methods involving nucleic acid amplification. In a preferred embodiment, a probe or primer of the invention can hybridize to a polynucleotide of the invention under stringent conditions. Probes and primers of the invention can optionally comprise a detectable label or reporter molecule, such as fluorescent molecules, enzymes, radioactive moiety (e.g., $^3$H, $^{35}$S, $^{125}$I, etc.), and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the invention. Probes and primers of the invention can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity so long as the probe or primer can hybridize under stringent conditions to a nucleotide sequence of a polynucleotide of the invention. In one embodiment, a probe or primer of the invention has 70% or greater, 75% or greater, 80% or greater, 85% or greater, 90% or greater, or 95% to 100% sequence identity with a nucleotide sequence of SEQ ID NO: 2 or SEQ ID NO: 3, or the complement thereof.

The subject invention also concerns an isolated mutant sorbitol dehydrogenase. In one embodiment, the mutant sorbitol dehydrogenase is a sorbitol dehydrogenase 1 of *Zea mays*. In a specific embodiment, a sorbitol dehydrogenase enzyme of the invention has an amino acid sequence as shown in SEQ ID NO: 1, or an enzymatically active fragment or variant thereof. A sorbitol dehydrogenase enzyme of the invention can be purified using standard techniques known in the art. In one embodiment, a polynucleotide of the invention encoding a sorbitol dehydrogenase is incorporated into a microorganism, such as *E. coli*, and the sorbitol dehydrogenase expressed in the microorganism and then its protein product isolated therefrom.

Polypeptides of the invention, and peptide fragments thereof, can be used to generate antibodies that bind specifically to a polypeptide of the invention, and such antibodies are contemplated within the scope of the invention. The antibodies of the invention can be polyclonal or monoclonal and can be produced and isolated using standard methods known in the art.

Polypeptide fragments according to the subject invention typically comprise a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, or 365 amino acids of SEQ ID NO: 1.

Polypeptide fragments of the subject invention can be any integer in length from at least about 25 consecutive amino acids to 1 amino acid less than the sequence shown in SEQ ID NO: 1. Thus, for SEQ ID NO: 1, a polypeptide fragment can be any integer of consecutive amino acids from about 25 to 365 amino acids. The term "integer" is used herein in its mathematical sense and thus representative integers include: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, and/or 365.

Each polypeptide fragment of the subject invention can also be described in terms of its N-terminal and C-terminal positions. For example, combinations of N-terminal to C-terminal fragments of about 25 contiguous amino acids to 1 amino acid less than the full length polypeptide of SEQ ID NO: 1 are included in the present invention. Thus, using SEQ ID NO: 1 as an example, a 25 consecutive amino acid fragment could correspond to amino acids of SEQ ID NO: 1 selected from the group consisting of 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, 26-50, 27-51, 28-52, 29-53, 30-54, 31-55, 32-56, 33-57, 34-58, 35-59, 36-60, 37-61, 38-62, 39-63, 40-64, 41-65, 42-66, 43-67, 44-68, 45-69, 46-70, 47-71, 48-72, 49-73, 50-74, 51-75, 52-76, 53-77, 54-78, 55-79, 56-80, 57-81, 58-82, 59-83, 60-84, 61-85, 62-86, 63-87, 64-88, 65-89, 66-90, 67-91, 68-92, 69-93, 70-94, 71-95, 72-96, 73-97, 74-98, 75-99, 76-100, 77-101, 78-102, 79-103, 80-104, 81-105, 82-106, 83-107, 84-108, 85-109, 86-110, 87-111, 88-112, 89-113, 90-114, 91-115, 92-116, 93-117, 94-118, 95-119, 96-120, 97-121, 98-122, 99-123, 100-124, 101-125, 102-126, 103-127, 104-128, 105-129, 106-130, 107-131, 108-132, 109-133, 110-134, 111-135, 112-136, 113-137, 114-138, 115-139, 116-140, 117-141, 118-142, 119-143, 120-144, 121-145, 122-146, 123-147, 124-148, 125-149, 126-150, 127-151, 128-152, 129-153, 130-154, 131-155, 132-156, 133-157, 134-158, 135-159, 136-160, 137-161, 138-162, 139-163, 140-164, 141-165, 142-166, 143-167, 144-168, 145-169, 146-170, 147-171, 148-172, 149-173, 150-174, 151-175, 152-176, 153-177, 154-178, 155-179, 156-180, 157-181, 158-182, 159-183, 160-184, 161-185, 162-186, 163-187, 164-188, 165-189, 166-190, 167-191, 168-192, 169-193, 170-

194, 171-195, 172-196, 173-197, 174-198, 175-199, 176-200, 177-201, 178-202, 179-203, 180-204, 181-205, 182-206, 183-207, 184-208, 185-209, 186-210, 187-211, 188-212, 189-213, 190-214, 191-215, 192-216, 193-217, 194-218, 195-219, 196-220, 197-221, 198-222, 199-223, 200-224, 201-225, 202-226, 203-227, 204-228, 205-229, 206-230, 207-231, 208-232, 209-233, 210-234, 211-235, 212-236, 213-237, 214-238, 215-239, 216-240, 217-241, 218-242, 219-243, 220-244, 221-245, 222-246, 223-247, 224-248, 225-249, 226-250, 227-251, 228-252, 229-253, 230-254, 231-255, 232-256, 233-257, 234-258, 235-259, 236-260, 237-261, 238-262, 239-263, 240-264, 241-265, 242-266, 243-267, 244-268, 245-269, 246-270, 247-271, 248-272, 249-273, 250-274, 251-275, 252-276, 253-277, 254-278, 255-279, 256-280, 257-281, 258-282, 259-283, 260-284, 261-285, 262-286, 263-287, 264-288, 265-289, 266-290, 267-291, 268-292, 269-293, 270-294, 271-295, 272-296, 273-297, 274-298, 275-299, 276-300, 277-301, 278-302, 279-303, 280-304, 281-305, 282-306, 283-307, 284-308, 285-309, 286-310, 287-311, 288-312, 289-313, 290-314, 291-315, 292-316, 293-317, 294-318, 295-319, 296-320, 297-321, 298-322, 299-323, 300-324, 301-325, 302-326, 303-327, 304-328, 305-329, 306-330, 307-331, 308-332, 309-333, 310-334, 311-335, 312-336, 313-337, 314-338, 315-339, 316-340, 317-341, 318-342, 319-343, 320-344, 321-345, 322-346, 323-347, 324-348, 325-349, 326-350, 327-351, 328-352, 329-353, 330-354, 331-355, 332-356, 333-357, 334-358, 335-359, 336-360, 337-361, 338-362, 339-363, 340-364, 341-365, 342-366. Similarly, the amino acids corresponding to all other fragments of sizes between 26 consecutive amino acids and 365 consecutive amino acids of SEQ ID NO: 1 are included in the present invention and can also be immediately envisaged based on these examples. Therefore, additional examples, illustrating various fragments of the polypeptides of SEQ ID NO: 1 are not individually listed herein in order to avoid unnecessarily lengthening the specification.

Polypeptide fragments comprising: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, and 365 consecutive amino acids of SEQ ID NO: 1 may alternatively be described by the formula "n to c" (inclusive), where "n" equals the N-terminal amino acid position and "c" equals the C-terminal amino acid position of the polypeptide. In this embodiment of the invention, "n" is an integer having a lower limit of 1 and an upper limit of the total number of amino acids of the full length polypeptide minus 24 (e.g., 366-24=342 for SEQ ID NO: 1). "c" is an integer between 25 and the number of amino acids of the full length polypeptide sequence (366 for SEQ ID NO: 1) and "n" is an integer smaller than "c" by at least 24. Therefore, for SEQ ID NO: 1, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, and 342; and "c" is any integer selected from the group consisting of: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, and 366 provided that "n" is a value less than "c" by at least 24. Every combination of "n" and "c" positions are included as specific embodiments of polypeptide fragments of the invention. All ranges used to describe any polypeptide fragment embodiment of the present invention are inclusive unless specifically set forth otherwise.

Fragments of a sorbitol dehydrogenase of the invention, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Polypeptide fragments can also be prepared by chemical synthesis or using host cells transformed with an expression vector comprising a polynucleotide encoding a fragment of a sorbitol dehydrogenase enzyme of the invention, for example, a sorbitol dehydrogenase that is a fragment of the amino acid sequence shown in SEQ ID NO: 1.

The subject invention also concerns cells transformed with a polynucleotide of the present invention encoding a sorbitol dehydrogenase of the invention. In one embodiment, the cell is transformed with a polynucleotide sequence comprising a sequence encoding the amino acid sequence shown in SEQ ID NO: 1, or an enzymatically active fragment or variant thereof. In a specific embodiment, the cell is transformed with a polynucleotide sequence shown in SEQ ID NO: 2 or 3, or a sequence encoding an enzymatically active fragment or variant of SEQ ID NO:1. In another embodiment, a mutant sdh polynucleotide comprises a mutant nucleotide sequence shown in FIG. 14B, or a fragment or variant of the nucleotide sequence.

Preferably, the polynucleotide sequence is provided in an expression construct of the invention. The transformed cell can be a prokaryotic cell, for example, a bacterial cell such as *E. coli* or *B. subtilis*, or the transformed cell can be a eukaryotic cell, for example, a plant cell, including protoplasts, or an animal cell. Plant cells include, but are not limited to, dicotyledonous, monocotyledonous, and conifer cells. In one embodiment, the plant cell is a cell from a *Zea mays* plant. Animal cells include human cells, mammalian cells, avian cells, and insect cells. Mammalian cells include, but are not limited to, COS, 3T3, and CHO cells.

An "antisense" nucleic acid sequence (antisense oligonucleotide) can include a nucleotide sequence that is complementary to a "sense" nucleic acid sequence encoding a protein, e.g., complementary to the coding strand of a double-stranded cDNA molecule or complementary to at least a portion of an Sdh gene. The antisense nucleic acid sequence can be complementary to an entire coding strand of a target sequence, or to only a portion thereof. In another embodiment, the antisense nucleic acid molecule is antisense to a "noncoding region" of the coding strand of a nucleotide sequence within the gene. An antisense oligonucleotide can be, for example, about 7, 8, 9, 10, 15, 20, 25, 30, 35, 40, 45, 50, 55, 60, 65, 70, 75, 80, or more nucleotides in length.

An antisense nucleic acid sequence can be designed such that it is complementary to the entire gene, but can also be an oligonucleotide that is antisense to only a portion of the gene. For example, the antisense oligonucleotide can be complementary to the region surrounding the translation start site of the target mRNA, e.g., between the −10 and +10 regions of the target gene nucleotide sequence of interest.

An antisense nucleic acid sequence of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid sequence also can be produced biologically using an expression vector into which a nucleic acid sequence has been subcloned in an antisense orientation (i.e., RNA transcribed from the inserted nucleic acid sequence will be of an antisense orientation to a target nucleic acid sequence of interest, described further in the following subsection).

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme encoding nucleotide sequences can be introduced into cells through gene-delivery mechanisms known in the art. A ribozyme having specificity for Sdh RNA can include one or more sequences complementary to the nucleotide sequence of at least a portion of one or more Sdh mRNA, and a sequence having known catalytic sequence responsible for mRNA cleavage (see U.S. Pat. No. 5,093,246 or Haselhoff et al. 1988). For example, a derivative of a Tetrahymena L-19 IVS RNA can be constructed in which the nucleotide sequence of the active site is complementary to the nucleotide sequence to be cleaved in the Sdh mRNA (see, e.g., U.S. Pat. Nos. 4,987,071; and 5,116,742). Alternatively, Sdh mRNA encoding an Sdh protein can be used to select a catalytic RNA having a specific ribonuclease activity from a pool of RNA molecules (see, e.g., Bartel et al. 1993).

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "short interfering RNA" ("siRNA") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA by the RNAi machinery or process. "mRNA", "messenger RNA", and "transcript" each refer to single-stranded RNA that specifies the amino acid sequence of one or more polypeptides. This information is translated during protein synthesis when ribosomes bind to the mRNA.

Single letter amino acid abbreviations are defined in Table 4.

TABLE 4

| Letter Symbol | Amino Acid |
| --- | --- |
| A | Alanine |
| B | Asparagine or aspartic acid |
| C | Cysteine |
| D | Aspartic Acid |

TABLE 4-continued

| Letter Symbol | Amino Acid |
| --- | --- |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Identification and Characterization of a Sorbitol Dehydrogenase-1 Gene in Maize High levels of expression in kernels initially drew attention to the maize Sorbitol dehydrogenase-1 gene (Sdh1). The Sdh1 transcripts were among the most abundant of any ESTs in libraries of maize kernels at 10 days after pollination (DAP) (MAIZEST database).

Figure 2:
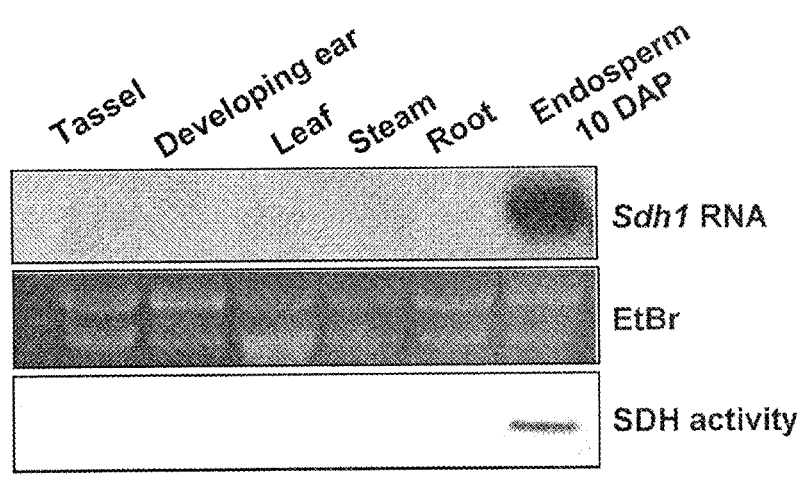
FIG. 2 shows sites of Sorbitol dehydrogenase-1 expression at the level of Sdh1 mRNA (upper panel) and SDH activity (lower panel), with Etbr loading controls in the mid panel. A 400-bp Sdh1 probe was used for RNA gel blot analyses. Activity assays in native PAGE were conducted with reaction buffer containing 68 mM sorbitol, 0.15 mM NAD, 0.18 mM nitro blue tetrazolium, 0.06 mM phenazine methasulfate, and 50 mM Tris-HCl, pH 8.0.
Figure 3:
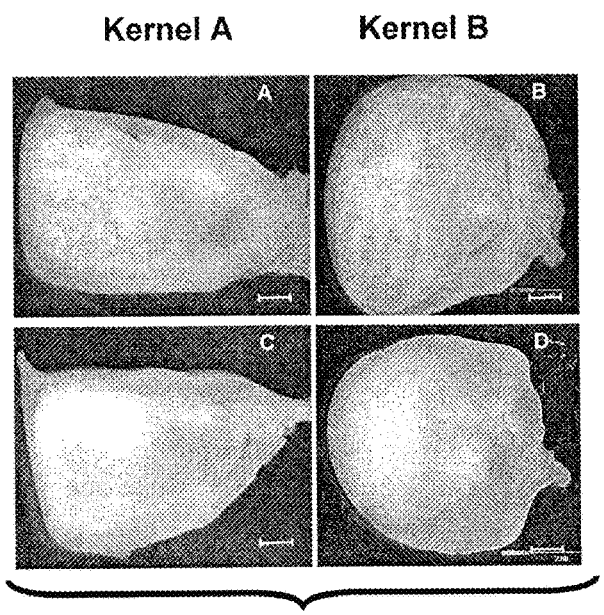
FIG. 3 shows SDH activity that was histochemically localized in longitudinally bisected fresh kernels (2 shown) at 20 DAP. One half of each kernel was exposed to reaction buffer with sorbitol for A & B, whereas sorbitol was omitted for control halves C & D. Blue color denotes activity.

Initial work (FIG. 2) showed high levels of expression for the Sdh1 gene and abundant activity of the SDH enzyme in endosperm of maize kernels at 10 DAP (days after pollination). In addition, Sdh1 expression was essentially endosperm-specific relative to other tissues examined. Further analysis indicated gradients of in situ SDH activity within the endosperm (FIG. 3), but little to no activity was evident for embryo tissue. This was perplexing given previous reports of abundant sorbitol in these structures (Carey et al., 1982; Doehlert et al., 1988), but subsequent data from de Sousa (see below) confirmed that there was minimal SDH activity or Sdh1 mRNA in embryos.

The possibility thus arose that sorbitol might move from endosperm to embryo (as diagramed in FIG. 4A), and there be metabolized by an as-yet-undefined means (low levels of SDH or a distinctive maize aldose reductase (AR)). Additional data also indicated that the reversible reaction of SDH could contribute to metabolic cycling with the potential to aid balance of key reactants and/or shuttle them from one site to another (As drawn in FIG. 4B). This possibility would include control of pool sizes for signaling molecules (like fructose) or redox control (as for NAD/NADH), and could operate in tissues other than seeds (e.g. floral apecies). To test the first portion of this scenario (sorbitol transfer and use in kernels), embryos were examined for their capacity to take-up and metabolize exogenous sorbtiol (FIG. 5). Sorbitol proved to be an excellent C-source for developing maize embryos, supporting their growth and germination as well as did sucrose, glucose, or fructose. Mannitol did not. Additional data from de Sousa (not shown) demonstrated that 13C-sorbitol micro-injected into the endosperm crown of intact, attached kernels, could move into developing embryos. Co-injection of water-soluble dye (aniline) did not follow the same path, indicating that simple diffusion could not account for the sorbitol transfer. Developing maize embryos can thus serve as effective sinks for sorbitol produced within the kernel.

Figure 6A:
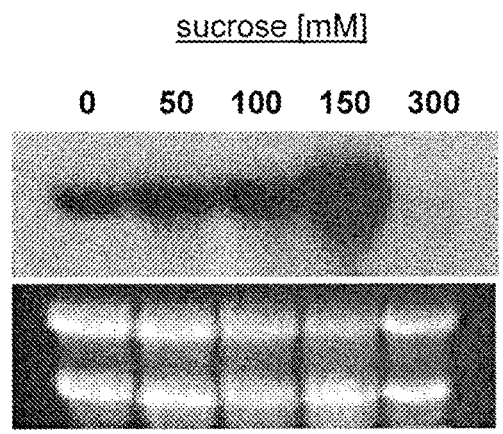
FIGS. 6A-6B show sucrose effects on levels of Sdh1 mRNA and SDH enzyme activity in maize kernels 8 hours after ear injections of sucrose at levels shown.
Figure 6B:
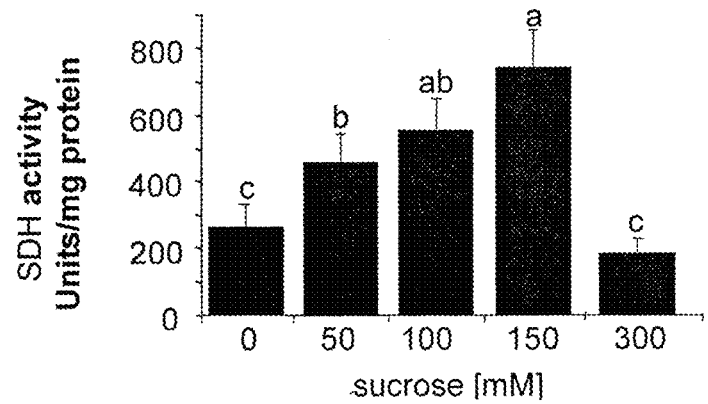
Figure 7:
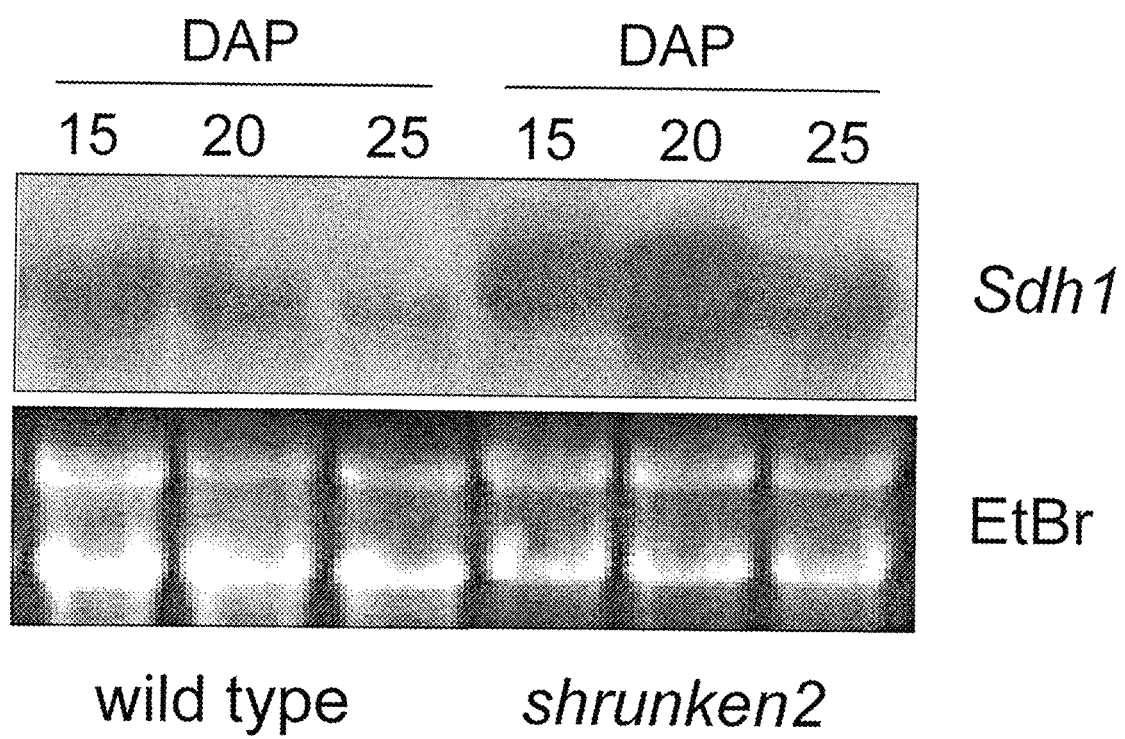
FIG. 7 shows elevated expression of Sorbitol dehydrogenase-1 (Sdh1) in the shrunken2 "sweet corn" mutant. RNA gel blot analysis during kernel development (15, 20 and 25 DAP) using a 400 pb SDH probe and showing an EtBr control.

Further analysis of the Sdh1 gene and its regulation showed that it was sugar-responsive (FIG. 6A), and that it is up-regulation by sucrose was significant at the level of SDH enzyme activity (FIG. 6B). Expression of the Sdh1 gene was also enhanced in the high-sugar environment of developing shrunken2 mutant "sweet corn" (FIG. 7).

Example 2—Identification of the Sdh1 Mutant

Figure 8:
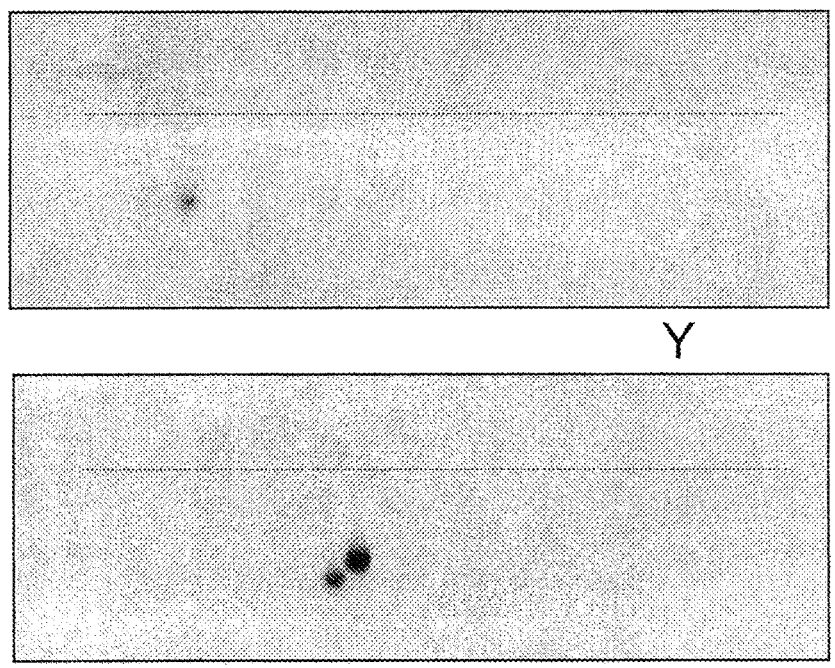
FIG. 8 shows a Mu insert in an sdh1 (Sorbitol dehydrogenase1) gene from a mutant isolated using the Uniform-Mu Maize Reverse Genetics Grid 1. Two points of intersection were observed. The sdh1 mutant was isolated from one, and the other is probably a related line. DNA traced to Plant 02S-1032-04.
Figure 8:
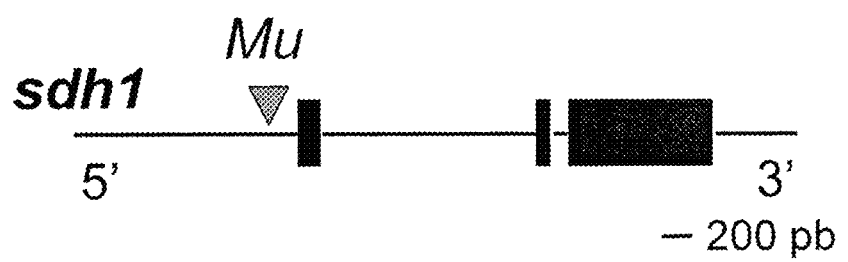

An sdh1 mutant was isolated from the Uniform-Mu maize population by screening the Reverse-Genetics Grids with gene-specific probes and primers. The Mu insertion was at the far 5' end of the sdh1 gene, immediately upstream of the start site (FIG. 8).

There are several important advantages to having obtained this mutant from the UniformMu population. The first of these is the uniform background, which is invaluable for comparisons to wildtype controls. The high degree of genetic similarity results from 9 generations of back-crossing to the W22 inbred (McCarty et al., 2005). The second advantage is the low mutant-load from previous generations, due to continual removal of any mutations, and repeated back-crossing to the inbred. The sdh1 mutant has been backcrossed 2 additional times. This maximizes the probability of a causal linkage between the observed phenotype and the sdh1 mutation. A third advantage is a capacity to fully-stabilize new mutants by selecting those lacking a functional transposase gene (using a color marker), and this has been completed for the sdh1 mutant.

Example 3

Figure 9A:
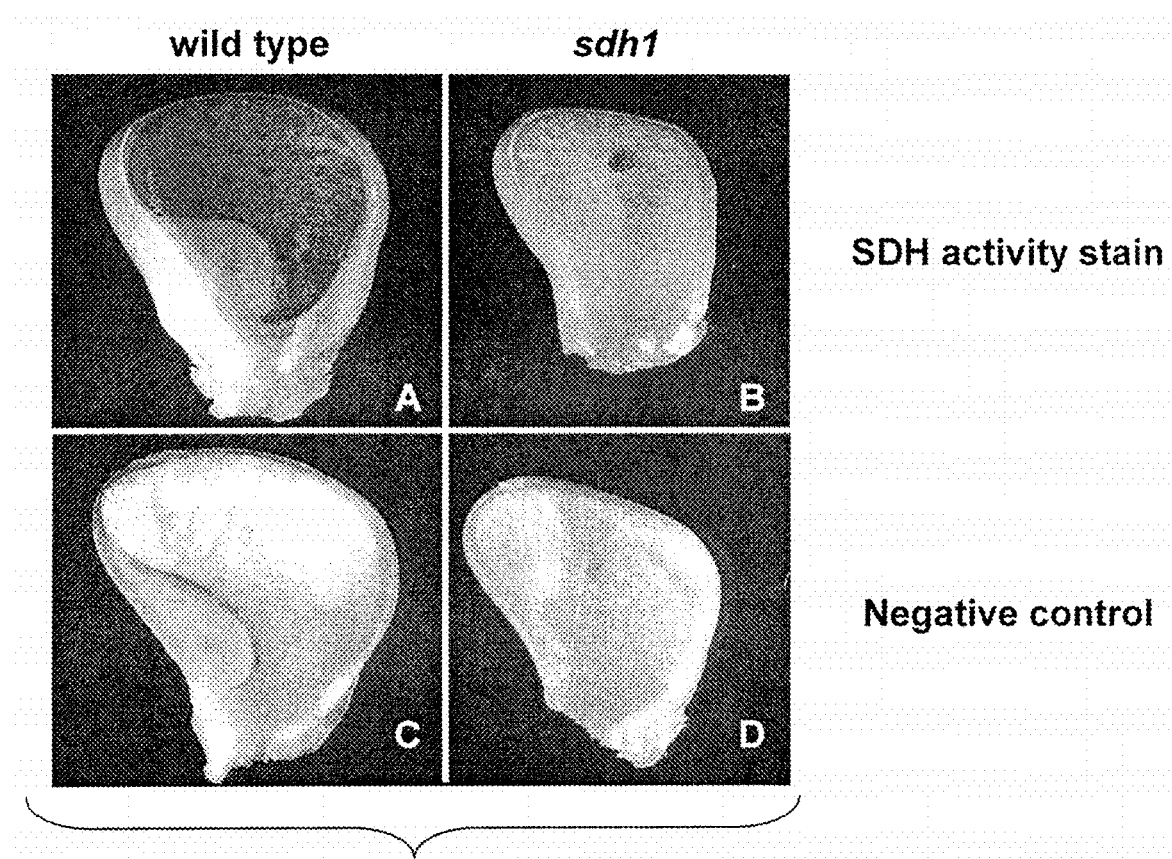
FIGS. 9A-9B show in situ activity of SDH in maize kernels (25 DAP)
Figure 9B:
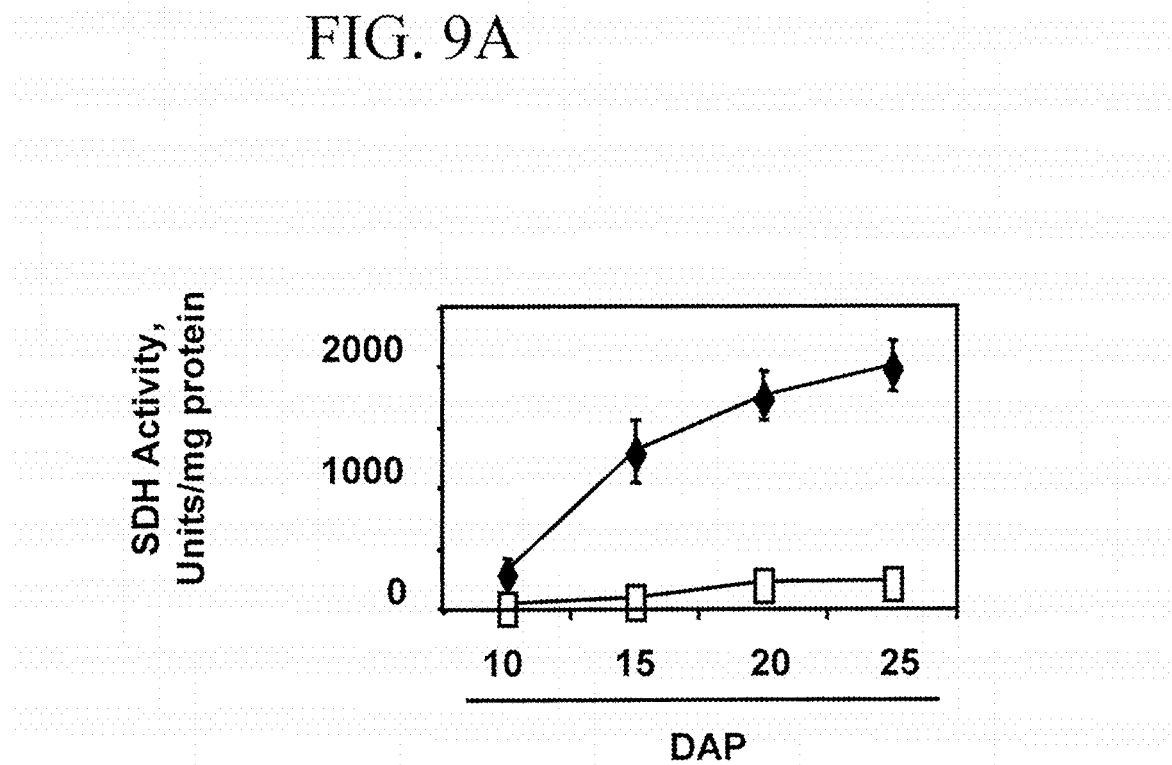
Figure 10A:
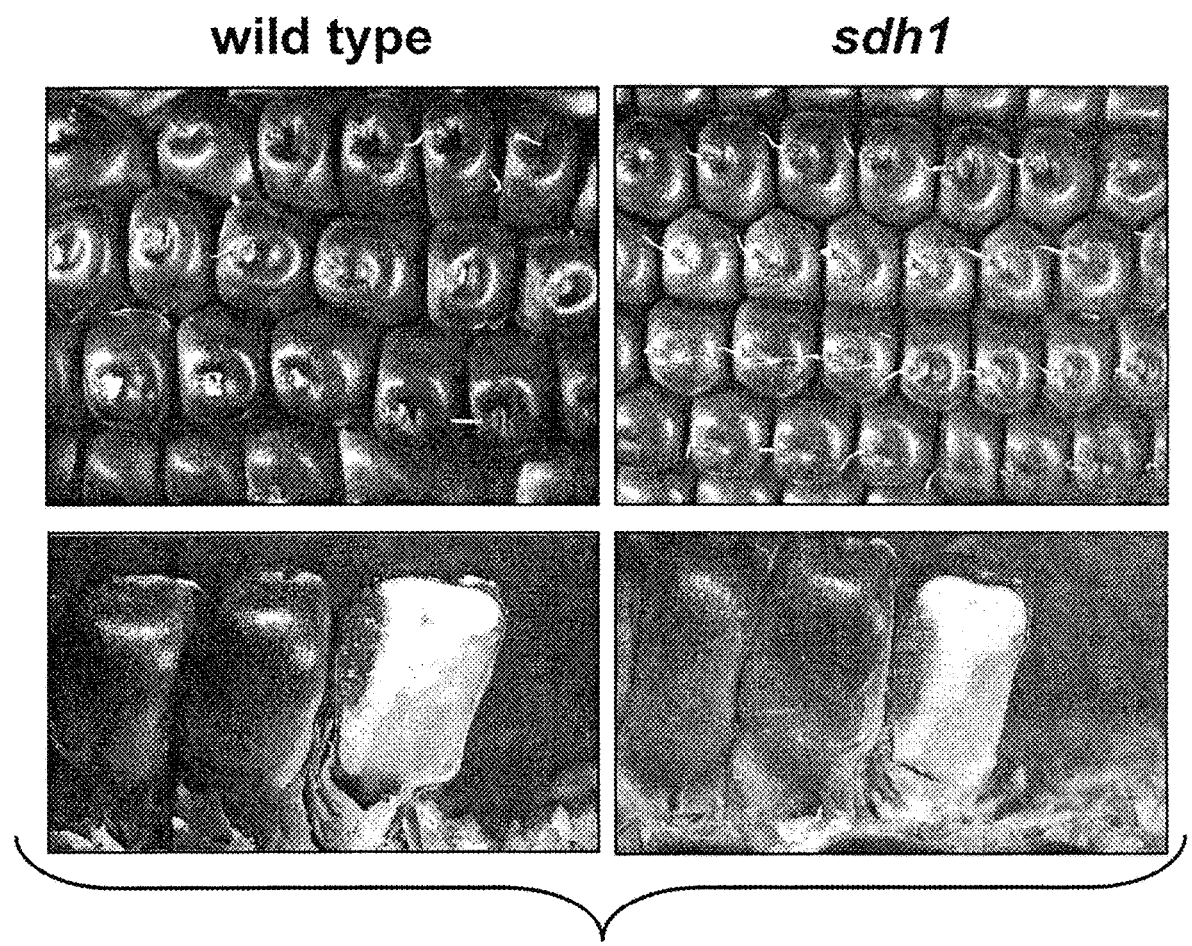
FIG. 10A shows maize ears and kernels of wildtype (left) and sdh1-mutant plants (right). Kernels were magnified 0.8×.
Figure 10B:
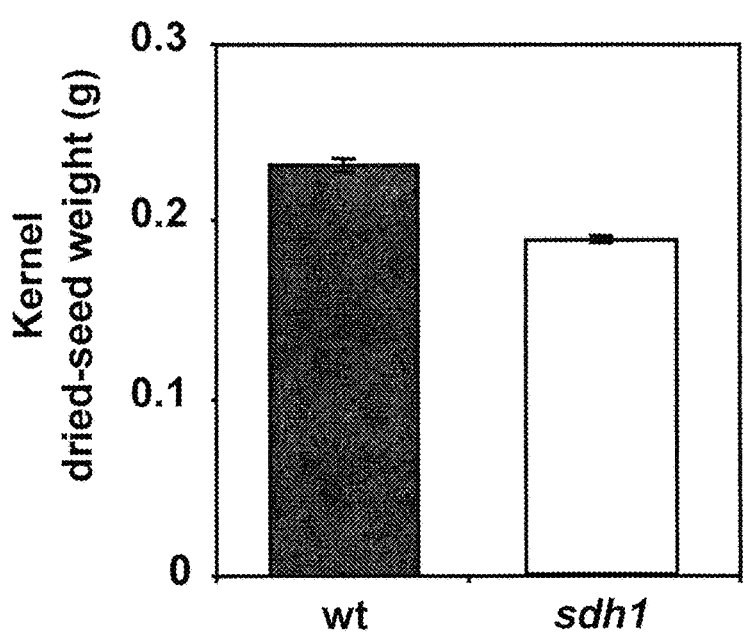
In FIG. 10B, dried-seed weight is shown for wildtype and sdh1-mutant kernels, all at 12% moisture (g). Additional results (not shown) were similar for subsequent studies of field- and greenhouse-grown plants (sdh1 kernels consistently 18 to 21% smaller).

FIG. 9 shows both the reduced size of sdh1 kernels and their deficiency in SDH activity (the latter by in situ activity stain and quantified assays). Maximal activity of SDH from mutant kernels remained less than 6% of that from wildtype. Dried-seed weight of sdh1 kernels was 21% less than that of wildtype ($p<0.001$ from first-year greenhouse and field studies) (FIG. 10). No differences were detectable between wildtype and heterozygous kernels although levels of Sdh1 mRNA were approximately 30% less (not shown). Similar results were observed when kernel size was compared on sdh1 and wildtype ears selected for similar overall kernel numbers.

Example 4

Data indicate that the number of maize kernels per ear can be increased by 2- to 3-fold using a dysfunctional gene for Sdh1 (Sorbitol dehydrogenase1). Analyses show that sdh mutants lacking a functional Sdh1 gene typically produced at least twice as many kernels per ear (FIG. 11). Kernel number also rose even if the dysfunctional sdh mutant gene was contributed by only one parent (sdh males increased kernel number by 2-fold, and sdh females by 3-fold) (FIG. 12A). These instances were notable in not necessarily reducing kernel size as was typical when both parents were sdh1 mutants. Combined effects of kernel size and kernel number were reflected in total ear weight (FIG. 12B), which was significantly increased when a single parent carried the mutant sdh gene. Mutant sdh males raised total ear weight by 30%, and sdh females enhanced ear weight by 85%. Similar increases were not evident when both parents were sdh mutants. A dysfunctional sdh1 gene can thus contribute to yield potential by increasing kernel number, especially when used in combination with a non-mutant parent. (Campos et al. [Pioneer Hi-Bred Intl] found that kernel number per ear, especially the second ear on the plant, was one of the greatest single plant components contributing to maize yields in the United States [unpublished data]).

The prominent effect of an sdh mutant gene from the maternal parent was further examined by comparing ears of all wildtype females to those of all sdh mutant females, regardless of the pollen parent utilized (wt or sdh) (FIG. 13). Results showed that contrasts between key features of wildtype and mutant ears were evident to the same degree for all wildtype and mutant mothers, even when male parents differed. Clear maternal influence was indicated for the number of kernels per ear (FIG. 13A, plus data above), kernels per row (FIG. 13B), and rows per ear (FIG. 13C). Despite the greater number of kernels per ear, the ear length was significantly reduced for sdh mutants receiving their own pollen (FIG. 13D). This extent of decrease in ear length was not evident for all sdh mothers, but cobs born on these females did have consistently shorter zones without developing kernels at their ear-tips (0.8 vs 2.2 cm, data not shown).

Figure 13A:
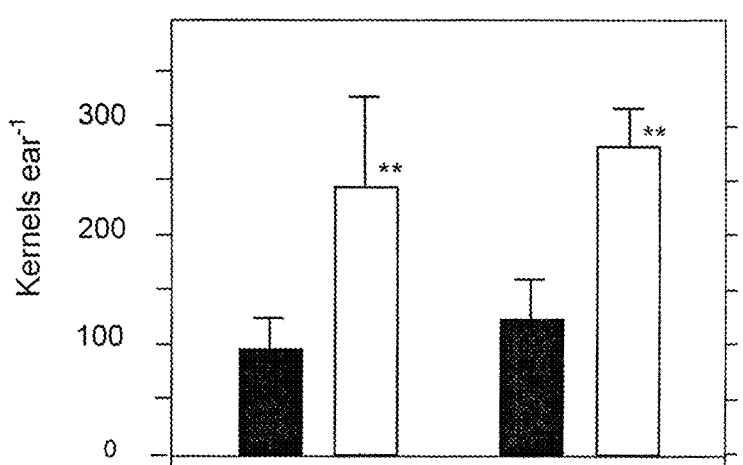
FIGS. 13A-13D show mutant and maternal effects on ear features of (wt) (shaded bars), Sdh mutant plants (unshaded bars), in an inbred W22 background. Bars at the left of each panel compare ears from all wt females to those of all sdh mutant females regardless of the pollen parent utilized (wt or sdh).
Figure 13B:
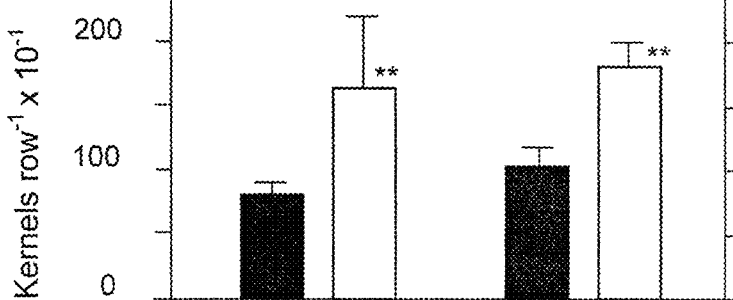
Figure 13C:
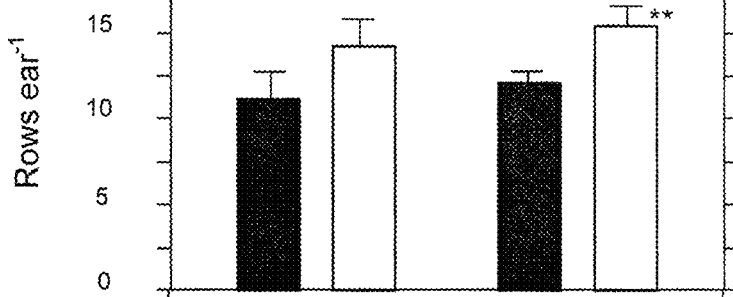
Figure 13D:
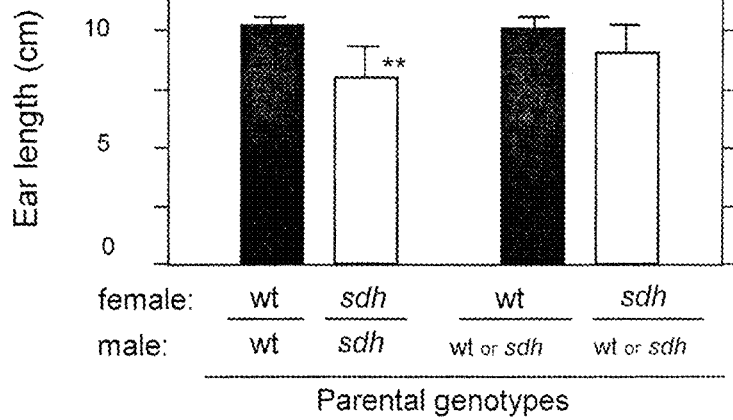

A particularly interesting contribution by the sdh mutation to kernel number is its effect on numbers of rows per ear, which increased an average of 25% for sdh mutant females (FIG. 13C). This was unexpected because row number is determined early in floral development, much before pollination, and prior to previously-detected expression of the Sdh1 gene (de Sousa et al., in preparation). Since the sdh mutation alters floral architecture more than 12 days before pollination, it must do so in minute primordial tissues of the newly-forming flower, where changes in gene expression could initially have been missed. The site and timing of this effect is also unexpected for a metabolic enzyme, but examples are emerging in maize and other systems for often-surprising contributions by sugar metabolism to changes in development. Examples include the influence of trehalose phosphate on floral architecture and other developmental features (Grennan, 2007), contributions by sugar pulses to induction of flowering in the apical meristem (Bernier and Perilleux), and complex effects of sugar metabolism on expression of genes for growth and development (Koch, 1996; Ohto et al., 2001; and Koch, 2004).

In addition, data presented here (FIGS. 14 and 15) indicate a link between effects of a dysfunctional sdh1 gene and its role in hybrid vigor of maize. We have determined that the "wildtype" sdh1 gene in the widely-used B73 inbred (and source of the reference maize genome sequence as of 2008) is actually a naturally-occurring sdh1 mutant If this sdh1 has limited function (as predicted by the site of its insert (see below) and data not shown), then this mutation may contribute significantly to the "combining ability" of B73 for hybrid corn production by increasing the number of kernels available for filling.

Figure 14A:
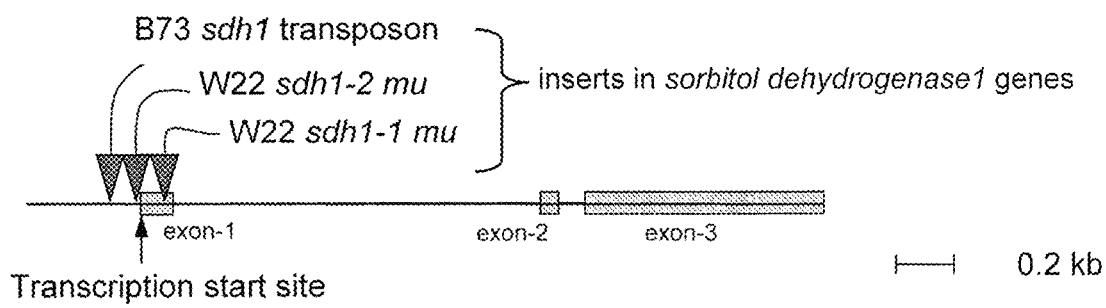
FIGS. 14A-14B show mutant sdh1 genes in B73 and W22 inbreds.
Figure 14B:
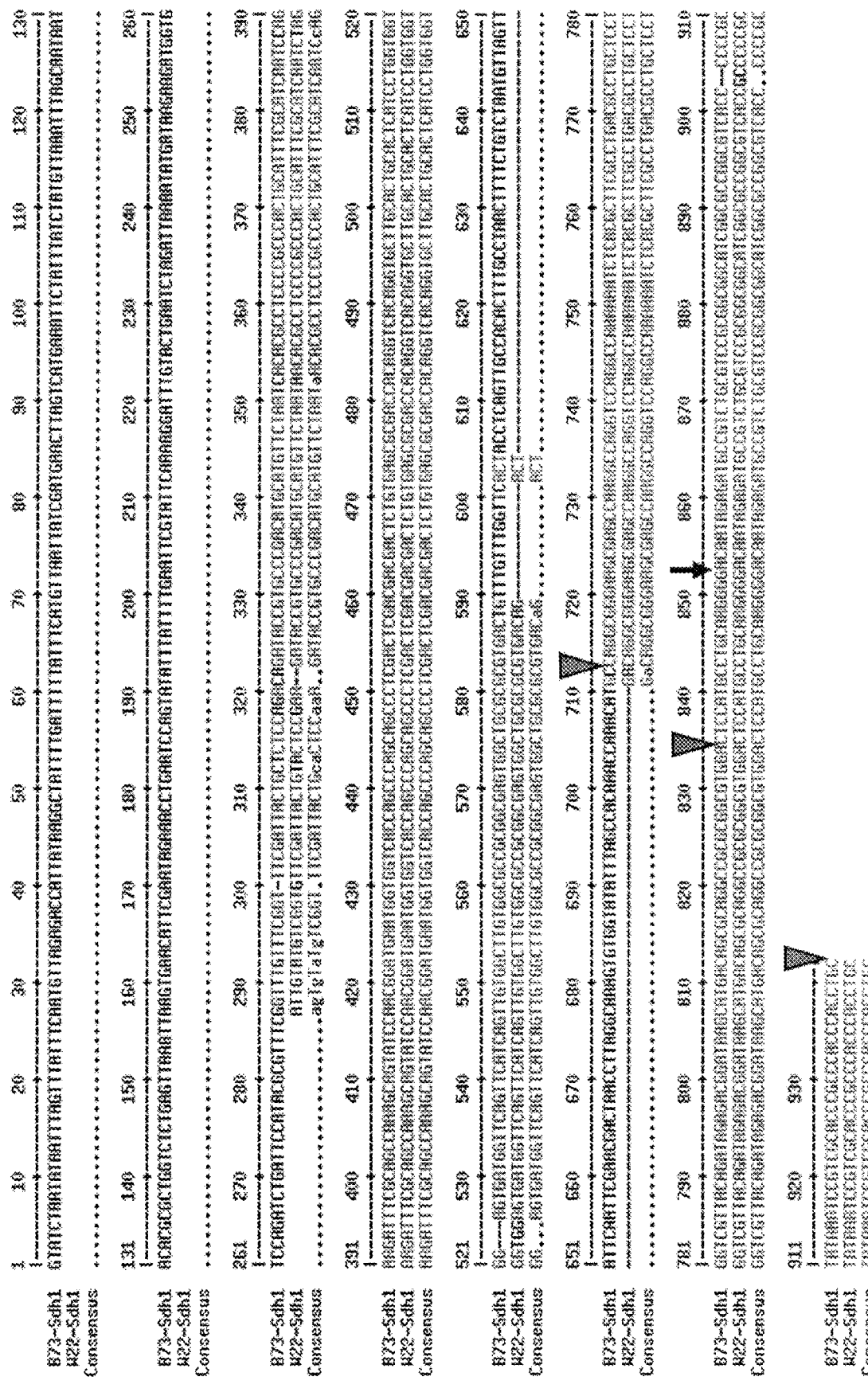

FIG. 14A shows the site of transposon inserts in the different sdh1 mutant genes. FIG. 14B compares the sequence of the B73 sdh1 mutant gene to that of a wildtype Sdh1 gene from a W22 inbred. The insert into the B73 gene is about 100 kb long and has characteristic features of a small transposable element (terminal inverted repeats at each end of the inserted sequence). The "wildtype" Sdh1 sequence available from GenBank is the mutated B73 sdh allele shown in FIG. 14B. Its mutant status was not evident until it was compared to a true wildtype gene lacking the transposable element disruption to its sequence. The original B73 sequence was submitted to GenBank by Sylvia de Sousa with a date for public release of Jul. 30, 2006. The GenBank accession number for this nucleotide sequence of sorbitol dehydrogenase is: bankit734791 DQ191049.

Figure 15:
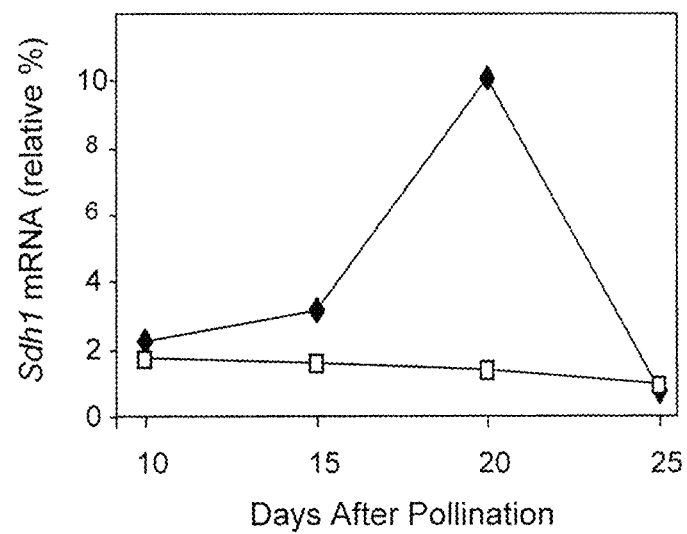
FIG. 15 shows Sdh1 (Sorbitol dehydrogenase1) expression at the mRNA level during development of B73 (open squares) and W22 (solid triangles) kernels.

Further evidence for dysfunction of a mutant sdh1 gene is shown in FIG. 15. Sorbitol dehydrogenase 1 gene expression is reduced to barely detectable mRNA levels throughout development of kernels from the B73 inbred, but not for those of the W22 inbred with its intact Sdh1 sequence. The B73 inbred has long been known for phenotypic features that resemble those conferred by the sdh1 mutant gene. These include a large number of somewhat smaller seeds, and a shorter, wider ear. These characters also appear to have contributed to the strength of B73 as a combinatorial partner in hybrid maize.

Example 5

Figure 16:
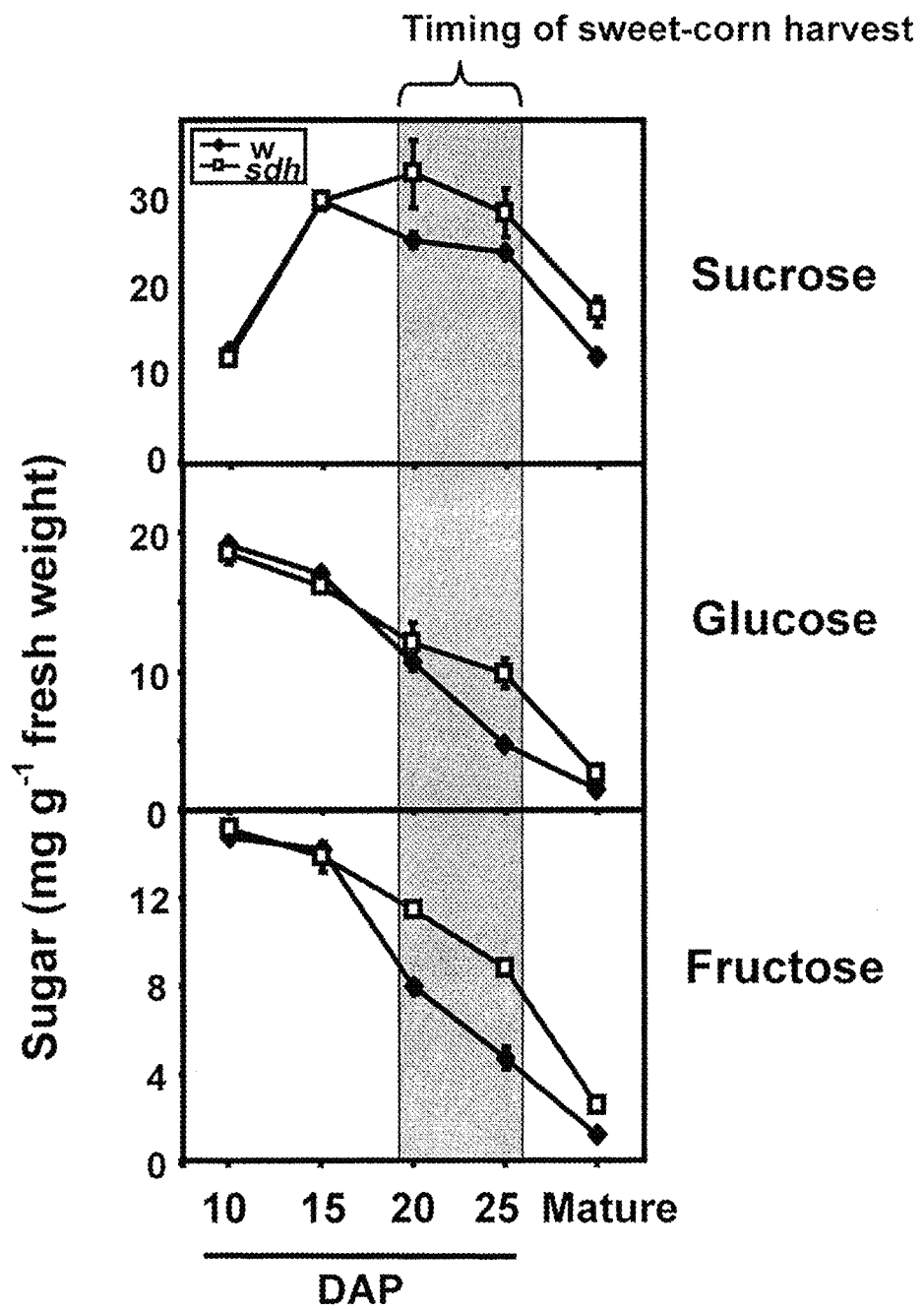
FIG. 16 shows elevated levels of sucrose, glucose, and fructose in sdh1 mutant kernels when compared to wildtype kernels at stages of development when sweet corn is typically harvested (between 20 and 25 DAP). For mature kernels, dried-seed weight was measured at 12% moisture (g). Error bars show SEMs of 3 biological replications. Soluble sugars were extracted three times from each sample using 80% ethanol (with xylose added as an internal control) at 80° C., and eluted with water. A 50-ul sample was injected into a Waters 2410 HPLC equipped with an refractive index detector. The sugars were separated on a Bio-Rad HPX-87C carbohydrate column.

FIG. 16 shows higher levels of sucrose, glucose, and fructose in sdh1-mutant kernels when these are compared to wildtype kernels at stages of development when sweet corn is typically harvested. Differences are not evident at kernel maturity, but persist during the sweet-corn harvest period (about 20 to 25 days after pollination (DAP)). Glucose and fructose, in particular, are about 2-fold greater in sdh1—than in wildtype kernels at 25 days after pollination (DAP). The possible usefulness of altered sdh1 expression in sweet corn lines is compatible with the observed up-regulation of this gene by sugars (noted earlier in FIGS. 6A and 6B) and in other, currently used sweet-corn lines (shown earlier for the shrunken2, sweet-corn mutant in FIG. 7).

Figure 17:
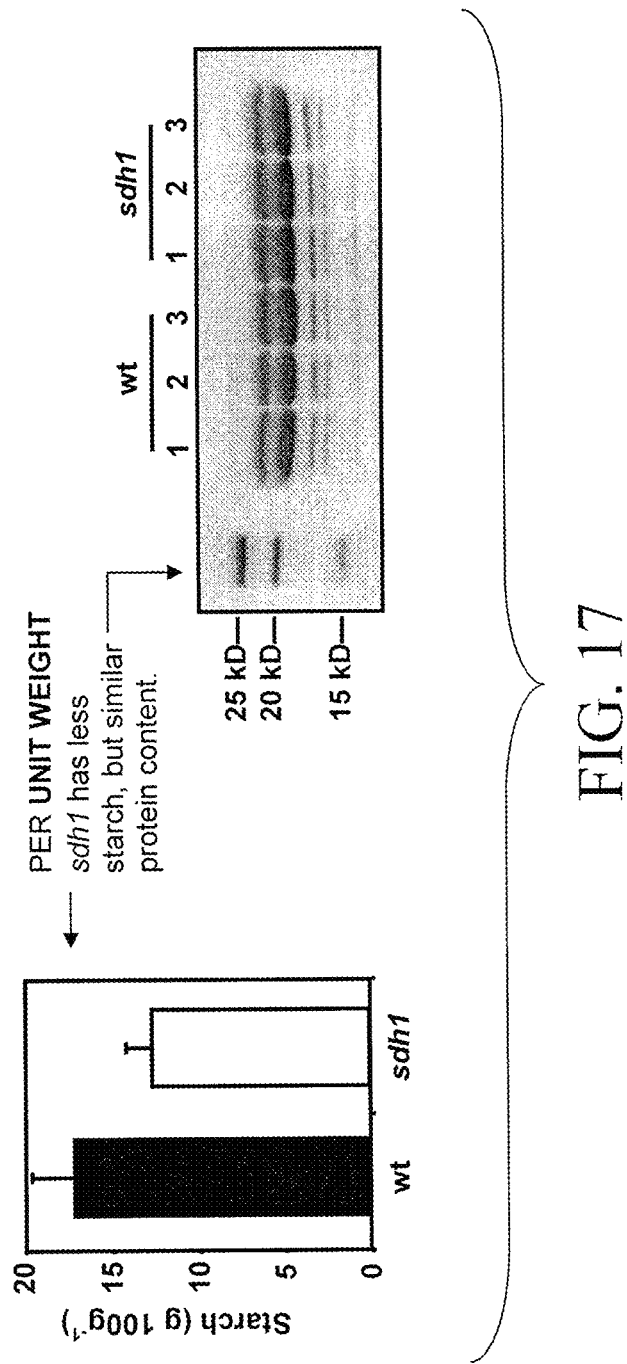
FIG. 17 shows kernel starch (g 100 $g^{-1}$ kernel) and zein content in wildtype and sdh1-mutant kernels. The sdh1 mutant kernels have about 25% less starch than wildtype at maturity. Both sdh1 and wildtype kernels have similar zein content and total protein (wt: 336.26±28.85; sdh1: 404.37±39.96). Dried seed weight of kernels was measured at 12% moisture (g). Error bars are SEMs of 3 replications.

FIG. 17 shows that the sdh1 mutant kernels have reduced starch levels at maturity (about 25% less). Starch reductions are typical of sweet-corn mutations, but the level of starch remaining here (and available for seed germination) is considerably greater than for most sweet corn lines. Protein content and zein composition of sdh1 kernels remained similar to those of wildtype kernels.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 6,642,435
U.S. Pat. No. 5,512,466
U.S. Pat. No. 5,625,136
U.S. Pat. No. 5,034,322
U.S. Pat. No. 5,589,610
U.S. Pat. No. 5,639,948
U.S. Pat. No. 6,462,185
U.S. Pat. No. 5,106,739
U.S. Pat. No. 6,455,760

U.S. Pat. No. 6,696,623
U.S. Pat. No. 5,661,017
U.S. Pat. No. 5,093,246
U.S. Pat. No. 5,116,742
U.S. Pat. No. 4,987,071
U.S. Pat. No. 5,589,618
U.S. Pat. No. 5,650,557
U.S. Pat. No. 5,872,216
U.S. Pat. No. 6,069,300
U.S. Pat. No. 6,403,863
U.S. Pat. No. 6,809,235
U.S. Pat. No. 7,312,378
U.S. Pat. No. 6,184,438
U.S. Pat. No. 6,969,783
U.S. Pat. No. 7,173,165
U.S. Published Application No. 20040078841
U.S. Published Application No. 20040067506
U.S. Published Application No. 20040019934
U.S. Published Application No. 20030177536
U.S. Published Application No. 20030084486
U.S. Published Application No. 20040123349
EPO Patent Published Application No. EP1528104
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
An, G. (1987) In: *Methods in Enzymology,* 153, eds. Wu, R. and Grossman, L. (Academic Press, New York), pp. 292-305.
Archbold, D. D. (1999). Carbohydrate availability modifies sorbitol dehydrogenase activity of apple fruit. Physiologia Plantarum 105:391-395.
Bagley, P. J. & Selhub, J. (2000) "Analysis of folate form distribution by affinity followed by reversed-phase chromatography with electrical detection" *Clin. Chem.* 46(3): 404-111.
Bartel, D. and Szostak, J. W. *Science* 261:1411-1418 (1993)
Basset, G. J., Quinlivan, E. P., Ravanel, S., Rébeillé, F., Nichols, B. P., Shinozaki, K., Seki, M., Adams-Phillips, L. C., Giovannoni, J. J, Gregory, J. F. III, Hanson A. D. (2004) "Folate synthesis in plants: the p-aminobenzoate branch is initiated by a bifunctional PabA-PabB protein that is targeted to plastids" *Proc. Natl. Acad. Sci. USA* 101(6):1496-1501.
Basset, G., Quinlivan, E. P., Ziemak, M. J., Diaz de la Garza, R., Fischer, M., Schiffmann, S., Bacher, A., Gregory, J. F. III & Hanson, A. D. (2002) "Folate synthesis in plants: the first step of the pterin branch is mediated by a unique bimodular GTP cyclohydrolase I" *Proc. Natl. Acad. Sci. USA* 99(19):12489-12494.
Bechtold, N., Ellis, J. & Pelletier, G. (1993) *C. R. Acad. Sci. Paris Life Sci.* 316:1194-1199.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology,* R. Wu, L. Grossman and K. Moldave [eds.] Academic Press, New York 100:266-285.
Bergmeyer, H. U. (1987). Methods of Enzymatic Analysis. VCH, Weinheim, Germany.
Bernier, G, and C Perilleaux (2005) A physiological overview of the genetics of flowering time control. *Plant Biotechnol J.* 3: 3-16.
Bieleski, R. L. (1982). Sugar alcohols. In Encyclopedia of Plant Physiology, New Series vol 13. Edited by Loewus, F. and Tanner, W. 158-192. Springer-Verlag, Berlin.
Bieleski, R. L., Redgwell. (1985). Sorbitol versus sucrose as photosynthesis and translocation products in developing apricot leaves. Aust. J. Plant. Physiol. 12:657-668.
Blakley, R. L. (1951). The metabolism and antiketogenic effects of sorbitol. Sorbitol dehydrogenase. Biochem. J. 49:257-271.
Blattner, F. R., Plunkett, G. III, Bloch, C. A., Perna, N. T., Burland, V., Riley, M., Collado-Vides, J., Glasner, J. D., Rode, C. K., Mayhew, G. F. et al. (1997) *Science* 277: 1453-1474.
Boggio, S. B., Palatnik, J. F., Heldt, H. W. & Valle, E. M. (2000) "Changes in amino acid composition and nitrogen metabolizing enzymes in ripening fruits of *Lycopersicon esculentum* Mill" *Plant Sci.* 159(1):125-133.
Bouis, H. E. (2002) "Plant breeding: a new tool for fighting micronutrient malnutrition" *J. Nutr.* 132(3):491S-494S.
Bradford, M. M. (1976) *Anal. Biochem.* 72:248-254.
Bruce, W. B., Quail, P. H. (1990). cis-Acting elements involved on photoregulation of an oat phytochrome promoter in rice. Plant Cell 2:1081-1089.
Callis, J., Fromm, M., Walbot, V. (1987). Introns increase gene expression in cultured maize cells. Genes Dev. 1:1183-1200.
Carey, E. E., Dickinson, D. B., Wei, L. Y., Rhodes, A. M. (1982). Occurrence of sorbitol in *Zea mays.* Phytochemistry 21: 1909-1911.
Centers for Disease Control and Prevention. (1996) *Morbidity and Mortality Weekly Report* 44 (SS-4):1-13.
Cheng, L., Zhou, R., Reidel, E. J., Sharkey, T. D., Dandekar, A. M. (2005). Antisense inhibition of sorbitol synthesis leads to up-regulation of starch synthesis without altering $CO_2$ assimilation in apple leaves. Planta 220:767-776.
Chorey, P. S., Zurawki, D. B. (1981). Callus formation from protoplasts of a maize cell line. Theor. Appl. Genet. 59:341-344.
Clancy, M. and Hannah, L. C. (2002) "Splicing of the maize Sh1 first intron is essential for enhancement of gene expression, and a T-rich motif increases expression without affecting splicing" *Plant Physiol.* 130(2):918-29.
Clough, S. J. & Bent, A. F. (1998) *Plant J.* 16:735-743.
Cossins, E. A. & Chen, L. (1997) "Folates and one-carbon metabolism in plants and fungi" *Phytochemistry* 45(3): 437-452.
Cossins, E. A. (2000) *Can. J. Bot.* 78:691-708.
de Boer, H. A., Comstock, L. J., Vasser, M. (1983) "The tac promoter: a functional hybrid derived from the trp and lac promoters" *Proc. Natl. Acad. Sci. USA* 80(1):21-25.
de Bree, A., van Dusseldorp, M., Brouwer, I. A., van het Hof, K. H. & Steegers-Theuniss-en, R. P. (1997) "Folate intake in Europe: recommended, actual and desired intake" *Eur. J. Clin. Nutr.* 51(10):643-660.
Deikman, J., Kline, R. & Fischer, R. L. (1992) *Plant Physiol.* 100:2013-2017.
DellaPenna, D. (1999) "Nutritional genomics: manipulating plant micronutrients to improve human health" *Science* 285(5426):375-379.
Diaz de la Garza, R. D. Quinlivan, E. P., Klaus, S. M. J., Basset, G. J. C., Gregory, J. F., Hansen, A. D. (2004) *Proc. Natl. Acad. Sci. USA* 101: 13720-13725.
Doehlert, D. C. (1987). Ketose activity in developing maize endosperm. Plant Physiol. 84:830-834.
Doehlert, D. C., Kuo, T. M. (1990). Sugar metabolism in developing kernels of starch deficient endosperm mutants of maize. Plant Physiol. 92:990-994.
Doehlert, D. C., Kuo, T. M., Felker, F. C. (1988). Enzymes of sucrose and hexose metabolism in developing kernels of two inbreds of maize. Plant Physiol. 86:1013-1019.

Doehlert, D. C., Smith, L. J., Duke, E. R. (1994). Gene expression during maize kernel development. Seed Science Research 4:299-305.

Duch, D. S., Browns, S. W., Wolf, J. H. & Nichol, C. A. (1984) "Biopterin cofactor biosynthesis: GTP cyclohydrolase, neopterin and biopterin in tissues and body fluids of mammalian species" Life Sci. 35:1895-1901.

Everard, J. D., Gucci, R., Kann, S. C., Flore, J. A., Loescher, W. H. (1994). Gas exchange and carbon partitioning in the leaves of celery (Apium graveolens L.) at various levels of root zone salinity. Plant Physiol. 106:281-292.

Evert, R. F., Russin, W. A. (1993). Structurally, phloem unloading in the maize leaf cannot be symplastic. American Journal of Botany 80:1310-1317.

Fell, D. A. (1998) "Increasing the flux in metabolic pathways: A metabolic control analysis perspective" Biotechnol. Bioeng. 58(2-3):121-124.

Forrest, H. S. & Van Baalen, C. (1970) "Microbiology of unconjugated pteridines" Annu. Rev. Microbiol. 24:91-108.

Frame, B. R., McMurray, J. M., Fonger, T. M., Main, M. L., Taylor, K. W., Torney, F. J., Paz, M. M., Wang, K. (2006). Improved Agrobacterium-mediated transformation of three maize inbred lines using MS salts. Plant Cell Rep. 25, 1024-34.

Freeling, M., Bennett, D. D. (1985). Maize Adh1. Annu. Rev. Genet. 19:297-323.

Freitas, F. A., Yunes, J. A., da Silva, M. J., Arruda, P., Leite, A. (1994) Structural characterization and promoter activity analysis of the □-kafirin gene from sorghum. Mol. Gen. Genet. 245:177-186.

Fukushima, T. & Nixon, J. C. (1980) "Analysis of reduced forms of biopterin in biological tissues and fluids" Anal. Biochem. 102(1):176-188.

Furtado, A. et al. (2002) "Tools for Use in the Genetic Engineering of Barley" Proceedings of the 10$^{th}$ Australian Barley technical Symposium, Canberra, ACT, Australia.

Gao, Z., Loescher, W. H. (2000). NADPH supply and mannitol biosynthesis. Characterization, cloning, and regulation of the non-reversible glyceraldehydes-3-phosphate dehydrogenase in celery leaves. Plant Physiol. 124:321-330.

Gao, Z., Maurousset, L., Lemoine, R., Yoo, S. D., van Nocker, S., Loescher, W. (2003). Cloning, expression, and characterization of sorbitol transporters from developing sour cherry fruit and leaf sink tissues. Plant Physiol. 131:1566-1575.

Geigenberger, P., Langenberger, S., Wilke, I., Heineke, D., Heldt, H. W., Stitt, M. (1993). Sucrose is metabolised by sucrose synthase and glycolysis within the phloem complex of Ricinus communis L. seedlings. Planta 190: 446-453.

Good, X. et al. (1994) "Reduced ethylene synthesis by transgenic tomatoes expressing S-adenosylmethionine hydrolase" Plant Molec. Biol. 26:781-790.

Goyer, A., Illarionova, V., Roje, S., Fischer, M., Bacher, A. & Hanson, A. D. (2004) "Folate biosynthesis in higher plants. cDNA cloning, heterologous expression, and characterization of dihydroneopterin aldolases" Plant Physiol. 135(1):103-111.

Green, J. M., Merkel, W. K., Nichols, B. P. (1992) "Characterization and Sequence of Escherichia coli pabC, the gene encoding aminodeoxychorismate lyase, a pyridoxal phosphate-containing enzyme" Journal of Bacteriology 174:5317-5323.

Gregory, J. F. III & Toth, J. P. (1988) "Chemical synthesis of deuterated folate monoglutamate and in vivo assessment of urinary excretion of deuterated folates in man" Anal. Biochem. 170(1):94-104.

Grennan, A K (2007) "The role of trehalose biosynthesis in plants" Plant Physiol. 144:3-5.

Grossowicz, N., Waxman, S. & Schreiber, C. (1981) "Cryoprotected Lactobacillus casei: an approach to standardization of microbiological assay of folic acid in serum" Clin. Chem. 27:745-747.

Hanson, A. D. & Gregory, J. F. III (2002) "Synthesis and turnover of folates in plants" Curr. Opin. Plant Biol. 5(3):244-249.

Haselhoff and Gerlach Nature 334:585-591 (1988).

Horne, D. W. & Patterson, D. (1988) "Lactobacillus Casei Microbiological Assay of Folic Acid Derivatives in 96-well Microtiter Plates" Clin. Chem. 34:2357-2359.

Hossain, T., Rosenberg, I., Selhub, J., Kishore, G., Beachy, R. & Schubert, K. (2004) "Enhancement of folates in plants through metabolic engineering" Proc. Natl. Acad. Sci. USA 101(14):5158-5163.

Huber, S. C., Akazawa, T. (1986). A novel sucrose synthase pathway for sucrose degradation in cultured sycamore cells. Plant Physiol. 81: 1008-1013.

Hwang, Y-S. et al. (2002) "Analysis of the Rice Endosperm-Specific Globulin Promoter in Transformed Rice Cells" Plant Cell Rep. 20:842-847.

Iida, M., Bantog, N. A., Yamada, K., Shiratake, K., Yamaki, S. (2004). Sorbitol and other sugar-induced expression of the NAD+-dependent sorbitol dehydrogenase gene in Japanese pear fruit. J. of American Soc. for Hort. Science 129:870-875.

James, M. G., Denyer, K., Myers, A. M. (2003). Starch synthesis in the cereal endosperm. Curr. Opin. Plant Biol. 6:215-222.

Jeong, Y. M., Mun, J. H., Lee, I., Woo, J. C., Hong, C. B., Kim, S. G. (2006). Distinct roles of the first introns on the expression of Arabidopsis profiling gene family members. Plant Physiol. 140:196-209.

Karlin S. and Altschul, S. F. (1990) "Methods for Assessing the Statistical Significance of Molecular Sequence Features by Using General Scoring Schemes" Proc. Natl. Acad. Sci. USA 87:2264-2268.

Karlin S. and Altschul, S. F. (1993) "Applications and Statistics for Multiple High-Scoring Segments in Molecular Sequences" Proc. Natl. Acad. Sci. USA 90:5873-5877.

Koch, K. (2004). Sucrose metabolism: regulatory mechanisms and pivotal roles in sugar sensing and plant development. Curr. Opin. Plant. Biol. 7: 235-46.

Koch, K. E., Avigne, W. T. (1990). Post-phloem, nonvascular transfer in citrus: Kinetics, metabolism, and sugar gradients. Plant Physiol. 93:1405:1416.

Koch, K. E., Nolte, K. D., Duke, E. R., McCarty, D. R., Avigne, W. T. (1992). Sugar levels modulate differential expression of maize sucrose synthase genes. Plant Cell 4:59-69.

Koch, K. E., Tsui, C. L., Schrader, L. E., Nelson, O. E. (1982). Source-sink relations in maize mutants with starch-deficient endospeon. Plant Physiol. 70:322-325.

Koch, K. E., Zeng, Y., Wu, Y., Avigne, W. T. (2000). Multiple paths of sugar-sensing and a sugar/oxygen overlap for genes of sucrose and ethanol metabolism. J. Exp. Bot. 51:417-427.

Koch, K E (1996) Carbohydrate-modulated gene expression in plants. Ann Rev Plant Physiol and Plant Mol. Bio. 47:509-540.

Kohashi, M. (1980) "Isolation of Six Unconjugated Pteridines From Soybean (Glycin max L. Tsurunoko) Seeds" *J. Biochem.* 87:1581-1586.

Kohashi, M., Tomita, K. & Iwai, K. (1980) *Agric Biol. Chem.* 44:2089-2094.

Konings, E. J., Roomans, H. H., Dorant, E., Goldbohm, R. A., Saris, W. H. & van den Brandt, P. A. (2001) "Folate intake of the Dutch population according to newly established liquid chromatography data for foods" *Am. J. Clin. Nutr.* 73(4):765-776.

Koziel, M. G., Carozzi, N. B. & Desai, N. (1996) "Optimizing expression of transgenes with an emphasis on post-transcriptional events" *Plant Mol. Biol.* 32(1-2):393-405.

Krishnaswamy, K. & Madhavan Nair, K. (2001) "Importance of folate in human nutrition" *Br. J. Nutr.* 85:S115-S124.

Laemmli, U. K. (1970) *Nature* 227:680-685.

Lemire, R. J. (1998) *JAMA* 259:558-562.

Lewin, B. (1985) *Genes II*, John Wiley & Sons, Inc., p. 96.

Lin, X. L. & White, R. H. (1988) "Structure of Solfapterin (erythro-Neopterin-3'-D-2-Deoxy-2-Aminoglucopyranoside) Isolated from the Thermophilic Archaebacterium *Sulfolobus solfataricus*" *J. Bacteriol* 170:1396-1398.

Lo Bianco, R., Rieger, M., Sung, S. J. S. (1999a). Activities of sucrose and sorbitol metabolizing enzymes in vegetative sinks of peach and correlation with sink growth rate. J. of American Soc. of Hort. Science 124:381-388.

Lo Bianco, R., Rieger, M., Sung, S. J. S. (1999b). Carbohydrate metabolism of vegetative and reproductive sinks in the late maturing peach cultivar 'Encore'. Tree Physiology 19:103-109.

Loescher, W. H. (1987). Physiology and metabolism of sugar alcohols in higher plants. Physiologia Plantarum 70:553-557.

Loescher, W. H., Everard, J. D. (1996). Sugar alcohol metabolism in sinks and sources. In Zamski, E., Shaffer, A. A., eds, Photoassimilate distribution in plant and crops: Source-sink relationships. Marcel Dekker, New York, 185-207.

Loescher, W. H., Marlow, G. C., Kennedy, R. A. (1982). Sorbitol metabolism and sink-source interconversions in developing apple leaves. Plant Physiol. 70:335-339.

Lucock, M. (2000) "Folic acid: nutritional biochemistry, molecular biology, and role in disease processes" *Mol. Genet. Metab.* 71(1-2):121-138.

Maniatis, T., E. F. Fritsch, J. Sambrook (1982) "*Nuclease Bal31*" *Molecular Cloning: A Laboratory Manual*, Cold Spring Harbor Laboratory, Cold Spring Harbor, N.Y.

Maret, W. Auld, D. S. (1998). Purification and characterization of human liver sorbitol dehydrogenase. Biochemistry 27:1622-1628.

Marini, I., Bucchioni, L., Borella, P. Corso, A. D., Mura, U. (1997). Sorbitol dehydrogenase form bovine lens: purification and properties. Arch. Biochem. Biophys. 340:383-391.

Mascarenhas, D., Mettler, I. J., Pierce, D. A., Lowe, H. W. (1990). Intron-mediated enhancement of heterologous gene expression in maize. Plant Mol. Biol. 15:913-920.

McCarty, D. R., A. M. Settles, M. Suzuki, B. C. Tan, S. Latshaw, T. Porch, K. Robin, J. Baier, W. T. Avigne, J. Lai, J. Messing, K. E. Koch, L. C. Hannah. (2005). Steady-state transposon mutagenesis in inbred maize. Plant J. 44: 52-61.

McElroy, D., Zhang, W., Cao, J., Wu, R. (1990). Isolation of an efficient actin promoter for use in rice transformation. Plant Cell 2:163-171.

Merlo, L., Passera, C. (1991). Changes in carbohydrate and enzyme levels during development of leaves of Prunus persica, a sorbitol synthesizing species. Physiologia Plantarum 83:621-626.

Milstien, S., Jaffe, H., Kowlessur, D. & Bonner, T. I. (1996) "Purification and Cloning of the GTP Cyclohydrolase I Feedback Regulatory Protein, GFRP" *J. Biol. Chem.* 271:19743-19751.

Molloy, A. M. & Scott, J. M. (2001) "Folates and prevention of disease" *Public Health Nutr.* 4(2B):601-609.

Moore, C. A., Li, S., Li, Z. Hong, S., Gu, H., Berry, R. J., Mulinare, J. & Ericson, J. D. (1997) *Am. J. Med. Gen.* 73:113-118

Morita, A., Umemura, T., Kuroyanagi, M., Futsuhara, Y., Perata, P., Yamagushi, J. (1998). Functional dissection of a sugar-repressed alpha-amylase gene (RamylA) promoter in rice embryos. FEBS lett 423:81-85.

Negm, F. B., Loescher, W. H. (1979). Detection and characterization of sorbitol dehydrogenase from apple callus tissue. Plant Physiol. 64:69-73.

Negm, F. B., Loescher, W. H. (1981). Characterization and partial purification of aldose-6-6-phosphate reductase (Alditol-6-phosphate:NADP 1-oxidoreductase) form apple leaves. Plant Physiol. 67:139-142.

Ng, K., Ye, R., Wu, X. C., Wong, S.-L. (1992). Sorbitol dehydrogenase from *Bacillus subtilis*. J. Biol. Chem. 267: 24989-24994.

Noiraud, N., Delrot, S., Lemoine, R. (2000). The sucrose transporter of celery. Identification and expression during salt stress. Plant Physiol. 122:1447-1455.

Nolte, K. D., Hendrix, D. L., Radin, J. W., Koch, K. E. (1995). Sucrose synthase localization during initiation of seed development and trichome differentiation in cotton ovules. Plant Physiol. 109:1285-1293.

Nolte, K. D., Koch, K. E. (1993). Companion-cell specific localization of sucrose synthase in zones of phloem loading and unloading. Plant Physiol. 101:899-905.

Nuccio, M. L. & Thomas, T. L. (1999) "ATS1 and ATS3: two novel embryo-specific genes in *Arabidopsis thaliana*" *Plant Mol. Biol.* 39(6):1153-1163.

Ohto, M-A, K Onai, Y Furukawa, E Aoki, A Takashi, and K Nakamura (2001) *Plant Physiol.* 127:252-261.

Pfeiffer, C. M. & Gregory, J. F. III (1996) "Enzymatic deconjugation of erythrocyte polyglutamyl folates during preparation for folate assay: investigation with reversed-phase liquid chromatography" *Clin. Chem.* 42(11):1847-1854.

Quinlivan, E. P., Roje, S., Basset, G., Shachar-Hill, Y., Gregory, J. F. III & Hanson, A. D. (2003) "The folate precursor p-aminobenzoate is reversibly converted to its glucose ester in the plant cytosol" *J. Biol. Chem.* 278(23): 20731-20737.

Ravanel, S., Cherest, H., Jabrin, S., Grunwald, D., Surdin-Kerjan, Y., Douce, R. & Rébeillé, F. (2001) "Tetrahydrofolate biosynthesis in plants: molecular and functional characterization of dihydrofolate synthetase and three isoforms of folylpolyglutamate synthetase in *Arabidopsis thaliana*" *Proc. Natl. Acad. Sci. USA* 98(26):15360-15365.

Sambrook, J., Fritsch, E. F. & Maniatis, T. (1989) *Molecular Cloning. A Laboratory Manual* (Cold. Spring Harbor Laboratory Press, New York), pp 14.18-14.19.

Scholl, T. O. et al. (2000) "Folic Acid: Influence on the Outcome of Pregnancy" *Am. J. Clin. Nutr.* 71S:1295S-1303S.

Scott, J., Rebeille, F. & Fletcher, J. (2000) "Folic acid and folates: the feasibility for nutritional enhancement in plant foods" *J. Sci. Food Agric.* 80:795-824.

Stea, B., Halpern, R. M., Halpern, B. C. & Smith, R. A. (1980) "Quantitative determination of pterins in biological fluids by high-performance liquid chromatography" *J. Chromatogr.* 188(2):(363-375.

Swedlund, B., Locy, R. D. (1993) "Sorbitol as the primary carbon source for the growth of embryogenic callus of maize" *Plant Physiol.* 103:1339-1346.

Sybesma, W., Starrenburg, M., Kleerebezem, M., Mierau, I., de Vos, W. M. & Hugenholtz, J. (2003a) "Increased production of folate by metabolic engineering of *Lactococcus* lactis" *Appl. Environ. Microbiol.* 69(6):3069-3076.

Sybesma, W., Starrenburg, M., Tijsseling, L., Hoefnagel, M. H. & Hugenholtz, J. (2003b) "Effects of cultivation conditions on folate production by lactic acid bacteria" *Appl. Environ. Microbiol.* 69(8):4542-4548.

Tieman, D. M., Clardi, J. A., Taylor, M. G. & Klee, H. J. (2001) "Members of the tomato LeEIL (EIN3-like) gene family are functionally redundant and regulate ethylene responses throughout plant development" *Plant J.* 26(1):47-58.

Van der Meer, I. M., Bovy, A. G. & Bosch, D. (2001) "Plant-based raw material: improved food quality for better nutrition via plant genomics" *Curr. Opin. Biotechnol.* 12(5):488-492.

Verma, I. C. (1978) *Lancet* 1:879-80.

Viswanathan, V. K., Green, J. M., Nichols, B. P. (1995) "Kinetic Characterization of 4-Amino-4-Deoxychorismate Synthase from *Escherichia coli*" *Journal of Bacteriology* 177(20):5918-5923.

Webb, K., Burley, J. W. A. (1962). Sorbitol translocation in apple. Science 137:766.

Wilson, S. D. & Horne, D. W. (1982) "Use of Glycerol-Cryoprotected *Lactobacillus Casei* for Microbiological Assay of Folic Acid" *Clin. Chem.* 28:1198-1200.

Win, T. (2000) *Dissertation, Institute of Chemistry and Biology of the Marine Environment* (Universität of Oldenburg, 26111 Oldenburg Germany), pp. 63-66.

Wu, C-L. et al. (1998) "Promoters of Rice Seed Storage Protein Genes Direct Endosperm-Specific Gene Expression in Transgenic Rice" *Plant and Cell Physiology,* 39(8):885-889.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Yang, T. T. et al. (1996) "Optimized Codon Usage and Chromophore Mutations Provide Enhanced Sensitivity with the Green Fluorescent Protein" *Nucleic Acid Research* 24(22):4592-4593.

Yim, J. J. et al. (1976) "Characteristics of Guanosine Triphosphate Cyclohydrolase I Purified From *Escherichia coli*" *J. Biol. Chem.* 251:5087-5094.

Yoneyama, T. & Hatakeyama, K. (1998) "Decameric GTP cyclohydrolase I forms complexes with two pentameric GTP cyclohydrolase I feedback regulatory proteins in the presence of phenylalanine or of a combination of tetrahydrobiopterin and GTP" *J. Biol. Chem.* 273(32):20102-20108.

Zhang, G. F., Maudens, K. E., Storozhenko, S., Mortier, K. A., Van Der Straeten, D. & Lambert, W. E. (2003) "Determination of total folate in plant material by chemical conversion into para-aminobenzoic acid followed by high performance liquid chromatography combined with on-line postcolumn derivatization and fluorescence detection" *J. Agric. Food Chem.* 51(27):7872-7878.

Campos, H., Cooper A., Habben, J. E., Edmeades, G. O, Schussler, J. R. (2004) "Improving drought tolerance in maize: a view from industry" *Field Crops Research* 90:19-34.

Lida, M., Bantog, N. A., Yamada, K., Shiratake, K., Yamaki, S. (2004). Sorbitol and other sugar-induced expression of the NAD+-dependent sorbitol dehydrogenase gene in Japanese pear fruit. J. of American Soc. for Hort. Science 129:870-875.

Nosarszewski, M., Clements, A. M., Downie, B., Archbold, D. D. (2004). Sorbitol dehydrogenase expression and activity during apple fruit set and early development. Physiologia Plant. 121: 391-398.

Oura, Y., Yamada, K., Shiratake, K., Yamaki, S. (2000). Purification and characterization of a NAD+-dependent sorbitol dehydrogenase form Japanese pear fruit. Phytochemistry 54: 567-572.

Plaxton, W. C., Podesta, F. E. (2006). The Functional Organization and Control of Plant Respiration. Critical Reviews in Plant Sciences 25:159-198.

Park, S. W., Song, K. J., Kim, M. Y., Hwang, J-H., Shin, Y. U., Kim, W-C., Chung, W-II. (2002). Molecular cloning and characterization of four cDNAs enconding the isoforms of NAD-dependent sorbitol dehydrogenase from the Fuji apple. Plant Science 162:513-519.

Rolletschek, H., Koch, K., Wobus, U., Borisjuk, L. (2005). Positional cues for starch/lipid balance in maize kernels and resource portioning to the embryo. Plant J. 42: 69-83.

Teo, G. Suzuki, Y., Uratsu, S. L., Lampinen, B., Ormonde, N., Hu, W. K., DeJong, T. M., Dandekar, A. M. (2006). Silencing leaf sorbitol synthesis alters long-distance partitioning and apple fruit quality. PNAS 103:18842-18847.

Touster, O., Shaw, D. R. D. (1962). Biochemistry of acyclic polyols. Physiol. Rev. 42:181-225.

Yamaguchi, H., Kanayama, Y., Yamaki, S. (1994). Purification and properties of NAD-dependent sorbitol dehydrogenase form apple fruit. Plant Cell Physiol. 35:887-892.

Yamada, K., Oura, Y., Mori, H., Yamaki, S. (1998). Cloning of NAD-dependent sorbitol dehydrogenase from apple fruit and gene expression. Plant Cell Physiol. 39: 1375-1379.

Zhou, R., Cheng, L., Wayne, R. (2003). Purification and characterization of sorbitol-6-phosphate phosphatase from apple leaves. Plant Science 165:227-232.

Zhou, R., Cheng, L., Dandekar, A. M. (2006). Down-regulation of sorbitol dehydrogenase and up-regulation of sucrose synthase in shoot tips of the transgenic apple trees with decreased sorbitol synthesis. J. Exp. Bot. 57:3647-3657.

Zimmermann, M. H., Ziegler, H. (1975). List of sugars and sugar alcohols in sieve-tube exudates. In: Transport in Plants 1: Phloem transport. Springer-Verlag Berlin Heidelberg, N.Y.

We claim:

1. A transgenic maize plant, plant tissue, or plant cell that comprises an insertion of a heterologous nucleotide sequence within the promoter of a sorbitol dehydrogenase (Sdh) plant gene, whereby expression of said gene is disrupted or inhibited, and wherein said maize plant, plant tissue, or plant cell exhibits decreased levels of Sdh enzyme or enzymatic activity and wherein said maize plant exhibits increased kernel number or kernel sugar content or both kernel number and kernel sugar content relative to levels in a corresponding maize plant that does not have said heterologous nucleotide inserted as a result of said disruption or inhibition of expression of said gene, and wherein said maize plant, plant tissue, or plant cell is a sweet corn comprising a shrunken2 mutation.

2. A method for increasing kernel number or kernel sugar content or both kernel number and kernel sugar content in an ear of a maize plant, wherein said maize plant is a sweet corn comprising a shrunken2 mutation, said method comprising introducing into the plant a heterologous nucleotide sequence that is inserted within the promoter of a sorbitol dehydrogenase (Sdh) gene of the plant, whereby expression of said gene is disrupted or inhibited, and wherein the plant exhibits decreased levels of Sdh enzyme or enzymatic activity as a result of said disruption or inhibition of expression of said gene relative to a maize plant that does not have said heterologous nucleotide introduced in the plant; and wherein said method further comprises pollinating and growing an ear of said maize plant for at least 20 days after pollination, wherein pollen for said pollinating is from a maize plant that does not comprise said heterologous nucleotide sequence, thereby increasing kernel number or kernel sugar content or both kernel number and sugar content in an ear of a maize plant.

3. A method for increasing kernel number or kernel sugar content or both kernel number and kernel sugar content in an ear of a maize plant, wherein said maize plant is a sweet corn comprising a shrunken2 mutation, said method comprising introducing into the plant a heterologous nucleotide sequence that is inserted within the promoter of a sorbitol dehydrogenase (Sdh) gene of the plant, whereby expression of said gene is disrupted or inhibited, and wherein the plant exhibits decreased levels of Sdh enzyme or enzymatic activity as a result of said disruption or inhibition of expression of said gene relative to a maize plant that does not have said heterologous nucleotide introduced in the plant; and wherein said method further comprises pollinating and growing an ear of said maize plant for at least 25 days after pollination, wherein pollen for said pollinating is from a maize plant that does not comprise said heterologous nucleotide sequence, thereby increasing kernel number or kernel sugar content or both kernel number and sugar content in an ear of a maize plant.

4. The method according to claim 3, wherein said maize plant is *Zea mays*.

5. The method according to claim 3, wherein the increase in kernel sugar content is exhibited in said maize plant at 20 to 25 days after pollination.

6. The method according to claim 3, wherein said increased sugar is sucrose, glucose, and fructose.

7. The method according to claim 3, wherein said increased sugar is sucrose.

8. The method according to claim 3, wherein said increased sugar is fructose.

9. The method according to claim 3, wherein kernel starch content at maturity of said kernel is decreased in said maize plant relative to a maize plant that does not have said heterologous nucleotide introduced in the plant.

10. The method according to claim 2, further comprising harvesting said ear at between 20 and 25 days after pollination.

11. The method according to claim 3, further comprising harvesting said ear at 25 days after pollination.

12. The method according to claim 3, wherein said nucleotide sequence is inserted within 140 base pairs upstream of the transcription start site of said Sdh gene.

13. The method according to claim 3, wherein said insertion blocks or inhibits the binding of a transcription factor or polymerase.

14. A method for increasing kernel fructose content in an ear of a maize plant, wherein said maize plant is a sweet corn comprising a shrunken2 mutation, said method comprising introducing into the plant a heterologous nucleotide sequence that is inserted within the promoter of a sorbitol dehydrogenase (Sdh) gene of the plant, whereby expression of said gene is disrupted or inhibited, and wherein the plant exhibits decreased levels of Sdh enzyme or enzymatic activity as a result of said disruption or inhibition of expression of said gene relative to a maize plant that does not have said heterologous nucleotide introduced in the plant, wherein said method comprises further pollinating and growing an ear of said maize plant for at least 20 days after pollination, and harvesting said ear at between 20 and 25 days after pollination, wherein pollen for said pollinating is from a maize plant that does not comprise said heterologous nucleotide sequence, thereby increasing kernel fructose content in an ear of a maize plant.

15. The method according to claim 14, wherein the increase in kernel sugar content is exhibited in said maize plant at 20 to 25 days after pollination.

16. The method according to claim 14, wherein said nucleotide sequence is inserted within 140 base pairs upstream of the transcription start site of said Sdh gene.

17. The method according to claim 14, wherein said insertion blocks or inhibits the binding of a transcription factor or polymerase.

18. The method according to claim 14, wherein kernel sucrose content is also increased.

19. The method according to claim 2, wherein said pollinating maize plant is not an sdh mutant.

20. The method according to claim 3, wherein said pollinating maize plant is not an sdh mutant.

* * * * *

UNITED STATES PATENT AND TRADEMARK OFFICE
CERTIFICATE OF CORRECTION

PATENT NO. : 10,813,324 B2
APPLICATION NO. : 12/599652
DATED : October 27, 2020
INVENTOR(S) : Karen Elaine Koch and Sylvia Morais De Sousa Page 1 of 1

It is certified that error appears in the above-identified patent and that said Letters Patent is hereby corrected as shown below:

In the Specification

<u>Column 8,</u>
Line 59, "sc/h" should read --*sdh*--.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*